United States Patent
Schmidt et al.

(10) Patent No.: US 11,690,978 B2
(45) Date of Patent: Jul. 4, 2023

(54) CATHETER FOR ULTRASOUND-GUIDED DELIVERY

(71) Applicant: Medtronic, Inc., Minneapolis, MN (US)

(72) Inventors: Elliot Schmidt, Minneapolis, MN (US); Joshua Packer, Blaine, MN (US); William R. Schildgen, Chisago City, MN (US)

(73) Assignee: Medtronic, Inc., Minneapolis, MN (US)

( * ) Notice: Subject to any disclaimer, the term of this patent is extended or adjusted under 35 U.S.C. 154(b) by 379 days.

(21) Appl. No.: 16/916,752

(22) Filed: Jun. 30, 2020

(65) Prior Publication Data
US 2021/0001085 A1    Jan. 7, 2021

Related U.S. Application Data

(60) Provisional application No. 62/870,365, filed on Jul. 3, 2019.

(51) Int. Cl.
*A61M 25/01*    (2006.01)
*A61B 17/34*    (2006.01)
(Continued)

(52) U.S. Cl.
CPC ..... *A61M 25/0108* (2013.01); *A61B 17/3468* (2013.01); *A61M 25/0009* (2013.01);
(Continued)

(58) Field of Classification Search
CPC ...... A61B 2090/378; A61B 2090/3925; A61B 2090/3966; A61B 2560/066; A61B 5/6853; A61B 5/6869; A61B 8/0841; A61B 90/39; A61M 2025/1075; A61M 2025/1079; A61M 2205/0238; A61M 25/0108; A61M 25/0147; A61M 25/1002
See application file for complete search history.

(56) References Cited

U.S. PATENT DOCUMENTS

| | | |
|---|---|---|
| 4,706,681 A | 11/1987 | Breyer et al. |
| 5,840,030 A | 11/1998 | Ferek-Petric et al. |

(Continued)

FOREIGN PATENT DOCUMENTS

| | | |
|---|---|---|
| EP | 2561898 A1 | 2/2013 |
| EP | 2644211 B1 | 12/2018 |

(Continued)

OTHER PUBLICATIONS

International Search Report and Written Opinion of International Application No. PCT/US2020/040617, dated Nov. 16, 2020, 14 pp.

*Primary Examiner* — Deanna K Hall
(74) *Attorney, Agent, or Firm* — Shumaker & Sieffert, P.A.

(57) ABSTRACT

A catheter including one or more echogenic members facilitate guiding the catheter to a selected locations within a patient using ultrasound imaging. The echogenic members may include expandable members, such as balloons, be positioned near a distal end of the catheter. The echogenic members include an echogenic material, such as a coating or a fluid, that is configured to enhance the diffuse sound scattering of the echogenic member. An expanded echogenic member is detectable using ultrasound imaging.

32 Claims, 11 Drawing Sheets

(51) Int. Cl.
  *A61M 25/00* (2006.01)
  *A61N 1/362* (2006.01)
  *A61B 5/00* (2006.01)
  *A61M 25/10* (2013.01)

(52) U.S. Cl.
  CPC ......... *A61M 25/0147* (2013.01); *A61B 5/686* (2013.01); *A61B 2560/066* (2013.01); *A61M 2025/1079* (2013.01); *A61M 2205/0238* (2013.01); *A61N 1/362* (2013.01)

(56) References Cited

U.S. PATENT DOCUMENTS

| | | |
|---|---|---|
| 6,506,156 B1 | 1/2003 | Jones et al. |
| 6,652,568 B1 | 11/2003 | Becker et al. |
| 7,850,610 B2 | 12/2010 | Ferek-Petric |
| 9,409,001 B2 | 8/2016 | Aggerholm et al. |
| 9,629,984 B2 | 4/2017 | Lysgaard et al. |
| 10,080,873 B2 | 9/2018 | Stapleton et al. |
| 10,806,907 B2 | 10/2020 | Elton |
| 10,842,556 B1* | 11/2020 | Tandri ................ A61B 18/1492 |
| 2007/0142770 A1 | 6/2007 | Rioux et al. |
| 2014/0039315 A1 | 2/2014 | Davies et al. |
| 2015/0306359 A1* | 10/2015 | Drasler ................ A61F 2/2433 |
| | | 606/191 |
| 2019/0125398 A1 | 5/2019 | Baldwin et al. |
| 2020/0214661 A1* | 7/2020 | Tropello ............. A61J 15/0088 |
| 2021/0001016 A1 | 1/2021 | Carroll et al. |
| 2021/0052861 A1 | 2/2021 | Fan et al. |

FOREIGN PATENT DOCUMENTS

| | | |
|---|---|---|
| EP | 2570150 B1 | 1/2019 |
| JP | 2007530168 A | 11/2007 |
| WO | 1993004727 A1 | 3/1993 |
| WO | 2005096797 A1 | 10/2005 |
| WO | 2014197886 A1 | 12/2014 |
| WO | 2015053737 A1 | 4/2015 |

* cited by examiner

CATHETER FOR ULTRASOUND-GUIDED DELIVERY

This application claims the benefit of U.S. Provisional Application Ser. No. 62/870,365, entitled "CATHETER FOR ULTRASOUND-GUIDED DELIVERY," and filed on Jul. 3, 2019, the entire content of which is incorporated herein by reference.

TECHNICAL FIELD

This disclosure relates to medical devices including elongated members introducible into a body of a patient.

BACKGROUND

Medical catheters may be advanced into vasculature of a patient to introduce a medical device, such as a medical electrical lead or implantable medical device (IMD), or therapeutic agent to a treatment site. Medical catheters may be advanced to the treatment site by a clinician applying an axial force to a portion of the catheter that is outside a body of the patient. Medical devices may be configured for delivery into a selected location within a patient, such as different chambers of a patient's heart, using such catheters. Medical imaging devices and techniques, such as fluoroscopy, may be used to aid in the positioning of medical catheters within the patient for the delivery of a medical device.

SUMMARY

The use of fluoroscopy imaging techniques to aid in the positioning of medical catheters includes several drawbacks, such as radiation exposure to patient and clinicians, clinician personal protective equipment requirements, such as lead vests or aprons, lack of soft tissue visibility using x-rays, and the need for large, expensive fluoroscopy or other medical imaging equipment. The disclosed delivery catheter includes markers that enable a clinician to use other imaging devices and techniques, such as ultrasound, to aid in the positioning of medical catheters at a selected location within a patient for the delivery of a medical device or therapeutic agent. As one example, a catheter may include at least one echogenic member positioned near a distal end of the catheter. The at least one echogenic member may be used to determine a position of the distal end of the catheter relative to a selected location, such as a particular region of the heart of a patient. Once positioned at the selected location, a medical device, such as, for example, a medical electrical lead may be advanced through a lumen of the catheter to the selected location.

In some examples, a catheter may include an elongate body and an echogenic member. The elongate body may extend along a longitudinal axis from a proximal end to a distal end and defining a lumen extending longitudinally within the elongate body. The elongate body may include a proximal portion and a distal portion. The echogenic member may be positioned on the distal portion of the elongate body. The echogenic member may be configured to controllably expand from a collapsed configuration to an expanded configuration, and may be configured to diffusely scatter a soundwave.

In some examples, a kit may include a catheter and a medical device. The catheter may include an elongate body and an echogenic member. The elongate body may extend along a longitudinal axis from a proximal end to a distal end and define a lumen extending longitudinally within the elongate body. The elongate body may include a proximal portion and a distal portion. The echogenic member may be positioned on the distal portion of the elongate body. The echogenic member may be configured to controllably expand from a collapsed configuration to an expanded configuration, and may be configured to diffusely scatter a soundwave. The medical device may be sized for delivery out of the distal end of the elongate body and configured for at least one of therapy delivery or sensing.

In some examples, a method of using a catheter may include advancing a catheter toward a selected location within a patient. The catheter may include an elongate body and an echogenic member. The elongate body may extend along a longitudinal axis from a proximal end to a distal end and define a lumen extending longitudinally within the elongate body. The elongate body may include a proximal portion and a distal portion. The echogenic member may be positioned on the distal portion of the elongate body. The method also may include expanding the echogenic member from a collapsed configuration to an expanded configuration, the echogenic member being configured to diffusely scatter a soundwave. The method also may include identifying at least one of a position, an orientation, or a trajectory of the distal portion of the catheter relative to the selected location based on a soundwave reflected by the echogenic member. The method also may include advancing a medical device through the lumen and out the distal end of the elongate body to the selected location for at least one of therapy delivery or sensing.

In some examples, a method of assembling a catheter may include forming an elongate body extending along a longitudinal axis from a proximal end to a distal end and defining a lumen extending longitudinally within the elongate body. The elongate body may include a proximal portion and a distal portion. The lumen may be configured to receive a medical device for at least one of therapy delivery or sensing. The method also may include forming, on the distal portion of the elongate body, an echogenic member configured to controllably expand from a collapsed configuration to an expanded configuration. The echogenic member may be configured to diffusely scatter a soundwave.

The details of one or more examples are set forth in the accompanying drawings and the description below. Other features, objects, and advantages will be apparent from the description and drawings, and from the claims.

DETAILED DESCRIPTION

Figure 1A:
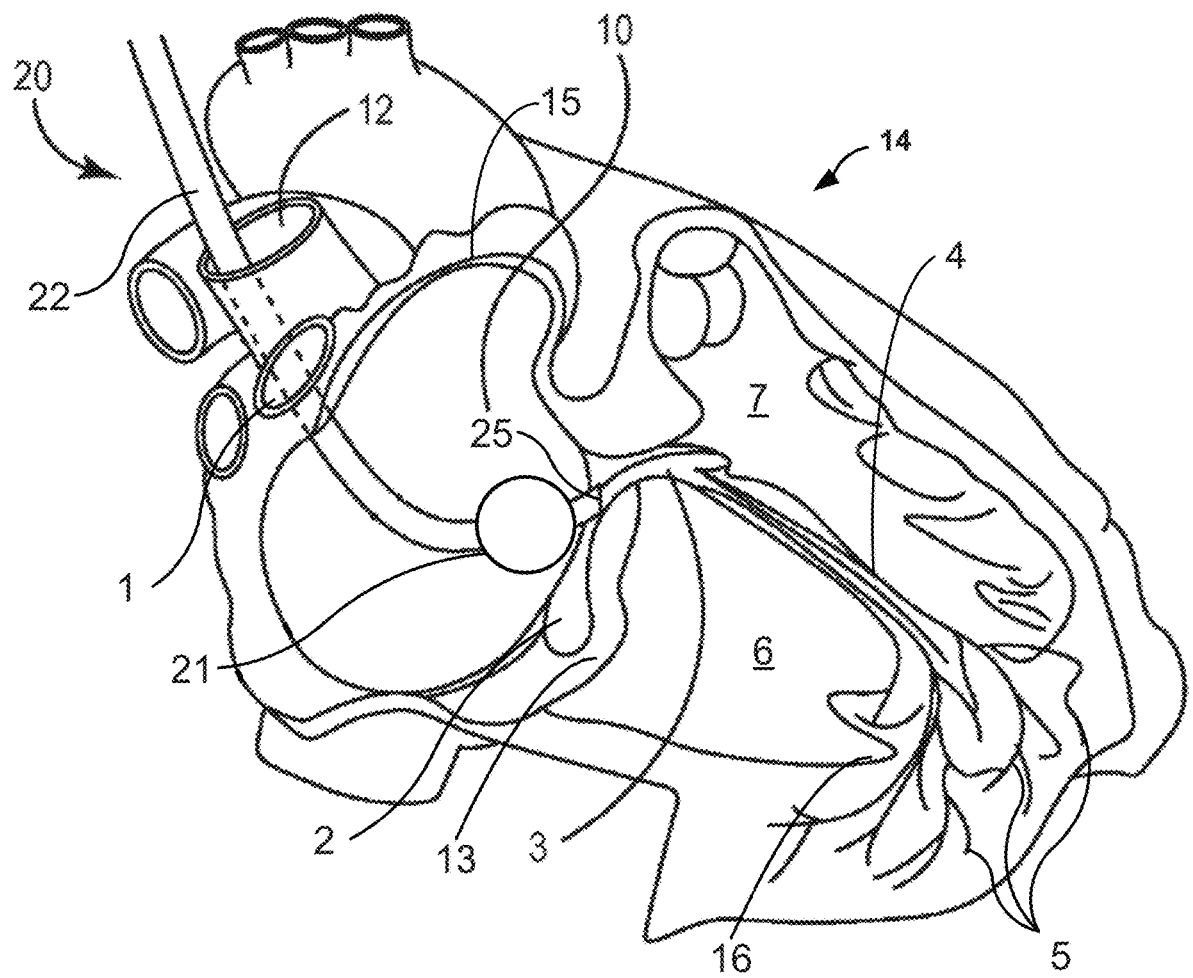
FIG. 1A is a conceptual diagram illustrating a right side of a heart in which a distal portion of an example catheter having an echogenic member is positioned.

The disclosure describes example systems, devices, and techniques for positioning catheters at a selected location within a patient to deliver a medical device or therapeutic agent (hereinafter described primarily in the context of delivery of a medical device) to the selected location. In general, the patient may be a human patient. However, in other examples, the patient may be a non-human patient. The selected location may generally include any site within the patient where stimulation, sensing, drug delivery, or therapy is desired. In some examples, the selected locations may include tissue suitable for ablation, such as ablation using cold, heat, electrical energy, or radiation. In some examples, the selected location includes a cardiac tissue, a coronary vein, or tissue suitable for pacing, which is not dead, damaged, or otherwise not operating within general anatomical norms. In some examples, the medical device may include a medical electrical lead, such as a brady lead or a tachy lead; a site selective medical electrical lead, such as His bundle or septal pacing lead; an implantable medical device (IMD), such as implantable pacing devices; or a left bundle branch medical electrical lead.

To overcome the drawbacks of some medical imaging techniques, such as fluoroscopy, as discussed above, ultrasound may be used to guide a delivery catheter to a selected location within a patient. However, positioning delivery catheters using ultrasound may be difficult due to the nature of ultrasound imaging, as described herein. The described delivery catheters are configured to facilitate guiding a catheter to a selected location using ultrasound. An example delivery catheter may include at least one echogenic member positioned near a distal end of the catheter. The echogenic member is configured to be visualized (e.g., detected) using ultrasound to provide an indication of the position and/or orientation of the distal end of the catheter. In some examples, an echogenic member may include an expandable member controllable between a collapsed and an expanded configuration. In the collapsed configuration, the expandable member may remain adjacent an external surface of the catheter, such that the diameter of the catheter is substantially unchanged by the collapsed expandable member. In this way, the echogenic member may not affect introduction of the catheter through vasculature of the patient. In the expanded configuration, the expandable member may be configured to provide an ultrasound target. For example, the expanded echogenic member may provide a larger target (e.g., relative to the collapsed echogenic member or catheter without an echogenic member) to enable a clinician to maintain at least a portion of the echogenic member within a viewing plane of the ultrasound to more accurately guide the catheter to the selected location.

In this disclosure, the example systems, devices, and techniques will be described with reference to delivering a medical electrical lead to a selected location in a heart. However, it will be understood that example systems, devices, and techniques of the present disclosure are not limited to delivering medical electrical leads to heart tissue. For example, example systems, devices, and techniques described herein may be used to deliver medical electrical leads to a coronary vein, to epicardial tissue, or other locations. Additionally, example systems, devices, and techniques described herein may be used to deliver medical electrical leads for neurostimulation therapy (e.g., spinal cord stimulation), deep brain stimulation, stimulation of one or more muscles, muscle groups or organs, and, generally, stimulation of tissue of a patient. Further, in some examples the example systems, devices, and techniques described herein can be used to deliver medical devices for dispensing a drug or other beneficial agent from an implanted or external drug delivery device. Additionally, in some examples the example system, devices, and techniques described herein can be used to deliver medical devices for ablating tissue using for example, cold, heat, electrical energy, or radiation. In short, the example systems, devices, and techniques described herein can find useful application in delivery of a wide variety of medical electrical leads or catheters for delivery of therapy to a patient or patient sensing.

FIG. 1A is a conceptual diagram illustrating distal portion 22 of an example catheter 20 positioned in the right side of a heart 14. Catheter 20 includes an echogenic member 21 disposed on distal portion 22 (e.g., near distal end 25) of catheter 20. Echogenic member 21 is configured to facilitate guiding catheter 20 to a selected location within heart 14 using ultrasound. Catheter 20 may be any suitable length and outer diameter. In some examples, a length of catheter may be within a range from about 30 centimeters (cm) to about 100 cm. In some examples, an outer diameter of catheter 20 may be less than about 28 French, or about 9.333 mm. As used herein, the term about may indicate a variation in a measurement (e.g., length, diameter, or the like) within tolerances of catheter manufacturing practices.

As illustrated in FIG. 1A, heart 14 has an anterior-lateral wall peeled back to present a portion of the intrinsic conduction system of heart 14 and chambers of a right atrium (RA) 10 and a right ventricle (RV) 6. Pertinent elements of the intrinsic conduction system of heart 14 may include a sinoatrial (SA) node 1, an atrioventricular (AV) node 2, a His bundle 3, a right bundle branch 4, and Purkinje fibers 5. SA node 1 is shown near the superior vena cava (SVC) 12 in the RA 10. An electrical impulse starting at the SA node 1 travels rapidly through tissue of RA 10 and tissue of a left atrium (not shown) to AV node 2. At AV node 2, the impulse slows to create a delay before passing on through His bundle 3, which branches, in an interventricular septum 7, into a right bundle branch 4 and a left bundle branch (not shown) and then, near RV apex 16, into Purkinje fibers 5. Flow of the electrical impulse creates an orderly sequence of atrial and ventricular contraction and relaxation to efficiently pump blood through heart 14.

Due to disease, injury, or natural defects, the intrinsic conduction system of heart 14 may no longer operate within general anatomical norms. In some examples, a cardiac pacemaker system can be implanted into a patient such that electrodes carried by an implantable medical electrical lead or a leadless implantable medical device (IMD) may be placed in an atrial appendage 15. The electrodes stimulate RA 10 downstream of SA node 1 and the stimulating pulse travels on to AV node 2, His bundle 3, and Purkinje fibers 5 to restore physiological contraction of the heart. However, if a patient has a defective AV node 2 pacing in atrial appendage 15 will not be effective, since the pacing site is upstream of AV node 2, e.g., atrioventricular block. For these or other reasons, a patient may have a cardiac pacemaker system implanted such that medical electrical leads are positioned at selected locations in RV apex 16, the His bundle 3 (as illustrated in FIG. 1A), the ventricular septum, or suitable locations in the left atrium or left ventricle. Navigating catheter 20 to deliver an electrical lead or a leadless implantable medical device (IMD) to a selected location within a patient requires medical imaging to visualize the location of catheter 20 relative to anatomy of heart 14. In some examples, catheter 20 may be inserted into heart 14 using a transvenous approach through the SVC 12 into the RA 10. In some examples, catheter 20 may be directed through the tricuspid valve 13 to RV 6. In some examples, catheter 20 may be tunneled from the right atrium, either through the interatrial septum and interventricular septum to the left ventricle or through the right ventricle and interventricular septum to the left ventricle. To overcome the drawbacks of some medical imaging techniques, such as fluoroscopy, as discussed above, ultrasound may be used to guide catheter 20 to a selected location within heart 14.

Positioning catheter 20 using ultrasound may be difficult due to the nature of ultrasound imaging. For example, the field of view of an ultrasound image may include a two-dimensional (2D) plane having a thickness within a range from about 2 millimeters (mm) to about 6 mm. Because the 2D plane of the ultrasound image is thin, e.g., relative to the volume of the heart 14 and/or the relative motion of catheter 20 as it is advanced to a selected location, it may be difficult for a clinician to maintain catheter 20 in the field of view, such as, for example, during motion caused by heart beats. Additionally, the resolution of ultrasound imaging may make it difficult to distinguish features smaller than about 1 mm to about 2 mm in diameter. Also, to visualize a structure using ultrasound, the structure must reflect (e.g., scatter) at least a portion of an emitted ultrasonic soundwave back to an ultrasound transducer. As used herein, visualizing a structure using ultrasound means to detect the structure by receiving at an ultrasound transducer a signal indicative of a reflection of ultrasonic sound waves emitted from the ultrasound transducer and processing the signal to generate an image indicative of the structure. In some examples, smooth surfaces of medical devices, such as catheter 20, may produce geometric scattering of an ultrasonic soundwave rather than diffuse scattering of the ultrasonic soundwave. Geometric scattering may reduce visualization of the medical device at angles off perpendicular. For these reasons, it may be difficult for a clinician to orient an ultrasound transducer to visualize catheter 20, to determine which portion of catheter 20 (or the medical device to be delivered) is within the field of view of the ultrasound, or both.

Echogenic member 21 may facilitate guiding catheter 20 to a selected location within heart 14 using ultrasound by increasing the size and diffuse reflection of at least a portion of catheter 20. To increase size, echogenic member 21 is configured to controllably expand from a collapsed configuration to an expanded configuration. In the collapsed configuration, a diameter of echogenic member 21 may be sufficiently small to pass through vasculature of a patient, such as equal to or less than about 28 Fr (9.333 mm), or less than about 9.5 mm. In the expanded configuration, a size and/or a shape of echogenic member 21 may be selected to improve visualization of echogenic member 21 using ultrasound. In some examples, a diameter of the echogenic member in an expanded configuration may be within a range from about 1 mm to about 30 mm, such as about 2 mm to about 15 mm. The diameter of echogenic member 21 may be selected to facilitate imaging of echogenic member 21 and/or facilitate maneuverability through vasculature or the heart of a patent. Echogenic member 21 may include a balloon, a self-expanding member, or controllably expanding member. The balloon may include, for example, an elastic material or an inextensible material defining an enclosed volume. The volume may be fluidly coupled to an inflation/deflation device configured to inflate and/or deflate the volume using a fluid, such as a liquid, a gas, a saline solution, or water. The self-expanding member or controllably expanding member may include, for example, a metal structure, a shape-memory alloy structure, or a stent-like metal structure that is expandable by deployment from a sheath or mechanical articulation.

Echogenic member 21 may include any suitable shape. For example, echogenic member 21 may include a spherical shape, a conical shape, a geometric shape, a tapered shape, or an irregular shape. In examples in which the echogenic member includes a tapered shape, the tapered shape may vary in radius of curvature and/or shape between its principal axes, such as, for example, a frustum, a cone, or an ellipse that is tapered on one end. For example, echogenic member 21 may include a distal end and a proximal end of echogenic member 21, each coupled to an external surface of catheter 20, echogenic member 21 tapered toward a longitudinal axis of catheter 20 at the distal end and/or the proximal end of echogenic member 21. The shape and size of echogenic member 21 may be selected based on a resolution (axial, lateral, or elevational) of a selected ultrasound imaging device, e.g., to remain visible given the resolution of a particular ultrasound imaging device. For example, in order to distinguish a tapered shape while imaging with a low resolution system, echogenic member 21 may include a more pronounced taper compared to imaging with a higher resolution system where a more subtle taper may be detectable.

Echogenic member 21 may be configured to diffusely scatter soundwaves, such as soundwaves having a frequency greater than about 20,000 Hertz (Hz), such as greater than about 1 MHz, such as within a range from about 1 MHz to about 20 MHz. For example, echogenic member 21 may include one or more materials configured to enhance the acoustic impedance and diffuse scattering characteristics of echogenic member 21. In some examples, echogenic member 21 may be defined by a sidewall the sidewall having an exterior surface and an interior surface defining an expandable lumen. The sidewall may include a polymeric material, such as a medical grade polymer, silicone, or polyurethane. In some examples, echogenic member 21 may include a reinforcing structure. The reinforcing structure may include an inextensible polymer or metal. The reinforcing structure may define coil, mesh, or pattern embedded in or disposed directly on the sidewall. The reinforcing structure may control a shape and/or size of the expanded configuration and/or the collapsed configuration of echogenic member 21. In some examples, echogenic member 21 may include an echogenic coating or be configured to be filled with an echogenic fluid. For example, an echogenic coating may be applied to an interior surface or an exterior surface of echogenic member 21, such as at least one of the sidewall or reinforcing structure, by, for example, spray-coating, dip-coating, or any suitable coating application process. In some examples, the echogenic coating may include an echogenic polymer, such as a polymeric matrix and a plurality of particles having a relatively higher acoustic impedance compared to the polymeric matrix, or microbubbles dispersed in the polymer, the microbubbles including a fluid having a relatively lower acoustic impedance compared to the polymeric matrix. The echogenic coating or echogenic fluid may enhance the definition of the silhouette of echogenic member 21 off perpendicular to the soundwave produced by an ultrasound imaging device. In this way, the echogenic coating or echogenic fill may improve the ability of a clinician to distinguish the full shape of echogenic member 21 and improve trackability of catheter 20.

In some examples, echogenic member 21 may include a radiopaque dye or radiopaque marker configured to enable visualization of echogenic member 21 using medical imaging techniques other than ultrasound, such as, for example, fluoroscopy.

Echogenic member 21 may be positioned any suitable distance from distal end 25 of catheter 20 to enable a clinician to determine the relative position of distal end 25. In some examples, echogenic member 21, e.g., a distal end of the echogenic member, may be within a range from about 0 mm (e.g., a distal end of echogenic member 21 may be flush or nearly flush within manufacturing tolerances relative to distal end 25 of catheter 20) to about 2 mm proximal to distal end 25. In other examples, echogenic member 21 may be greater than 2 mm proximal to distal end 25. In some examples, echogenic member 21 may be positioned at other locations on catheter 20, such as, for example, adjacent preformed curves or articulating portions of catheter 20. In some examples, a distal end or a proximal end of echogenic member 21 may differ when echogenic member 21 is in the collapsed configuration and the expanded configuration. For example, when in the collapsed configuration, a distal end of echogenic member 21 may not extend past distal end 25 of catheter 20, and when in the expanded configuration, echogenic member 21 extend past distal end 25 of catheter 20.

As discussed above, catheter 20 may facilitate advancement of the catheter 20 through vasculature of a patient. For example, catheter 20 may comprise a flexible, biocompatible material such as, for example, silicone or polyurethane. In some examples, catheter 20 may include a preformed curve. For example, upon advancing into RA 10, catheter 20 may begin to regain its preformed curve. In some examples, catheter 20 is a steerable catheter. In some examples, catheter 20 is a guidable catheter and includes a lumen for receiving a guide wire to assist with advancing the catheter 20 at least a portion of a distance to a selected location within heart 14. In some examples, catheter 20 includes features that allow it to effectively transfer force applied to a proximal end, e.g., via a handle assembly (not shown), of catheter 20 into motion of a distal end 25 of catheter 20. For example, distal portion 22 may include multiple curves proximate distal end 25 to facilitate guiding distal end 25 to a selected location. In some examples, the multiple curves may be formed by an articulating segment adjustable by, for example, a pull wire that can be manipulated by a control member at the handle assembly, a preformed curve segment, or other features configured to shape a length of distal portion 22.

In some examples, catheter 20, such as, for example, a portion of echogenic member 21, may be configured to emit a gas, such for example, carbon dioxide, from or near distal end 25 of catheter 20 or echogenic member 21. The emission of the gas may, in some examples, improve ultrasound visualization of distal end 25 of catheter 20. For example, the gas may have a lower acoustic impedance compared to the surrounding blood and/or tissue. The lower acoustic impedance may produce a stronger ultrasound signal compared to a catheter that is not configured to emit a gas. In some examples, the inflation/deflation device configured to inflate echogenic member 21 also may be configured to elute the gas from catheter 20. As one example, the inflation/deflation device may include a single inflation lumen that may be used to both inflate echogenic member 21 and elute gas from catheter 20. Use of a single inflation lumen to perform both functions may reduce the circumference of catheter 20 compared to a catheter using two separate lumens to perform these functions.

In some examples, the inflation/deflation device may further include a pressure release check valve. The pressure check valve may be disposed at or near distal end 25 of catheter 20 or at echogenic member 21. The pressure check valve may be configured to reduce deflation of echogenic member 21 and/or reduce ingress of blood into the inflation/deflation device and/or echogenic member 21. In some examples, the pressure check valve also may be configured to reduce over-pressurization of echogenic member 21. In operation, echogenic member 21 may be filled via the inflation/deflation device (e.g., the inflation lumen) with a fluid (e.g., either gas or liquid). Next, in order to begin the gas elution, a gas source is attached to the inflation/deflation device and pressure is applied to the inflation/deflation device. The inflation/deflation device is pressurized until the pressure is greater than the rating of the pressure release valve at which point the pressure valve opens and gas begins eluting into an area around catheter 20, e.g., out distal end 25 of catheter.

In some examples, catheter 20, such as, for example, a portion of echogenic member 21, may include a piezoelectric transducer configured to, in response to an electrical signal, emit a pressure wave. The pressure wave may include, for example, an ultrasound having a frequency up to about 20 MHz. The emission of the pressure wave may improve ultrasound visualization of distal end 25 of catheter 20 compared to a catheter without a piezoelectric transducer. In some examples, the piezoelectric transducer may be electrically coupled, e.g., via one or more conductive wires, to a transponder circuit and a power supply. The transponder circuit and/or the power supply may be disposed, for example, within a portion of catheter 20 or external to catheter 20. In some examples, electrically conductive wires coupling the piezoelectric transducer to the transponder circuit and/or the power supply may extend within a jacket of catheter 20, through one or more wiring lumens, and/or through an inflation lumen of the inflation/deflation device. Wires disposed within the inflation lumen may simplify manufacturing compared to running wires through additional lumens or within the jacket of catheter 20.

Figure 1B:
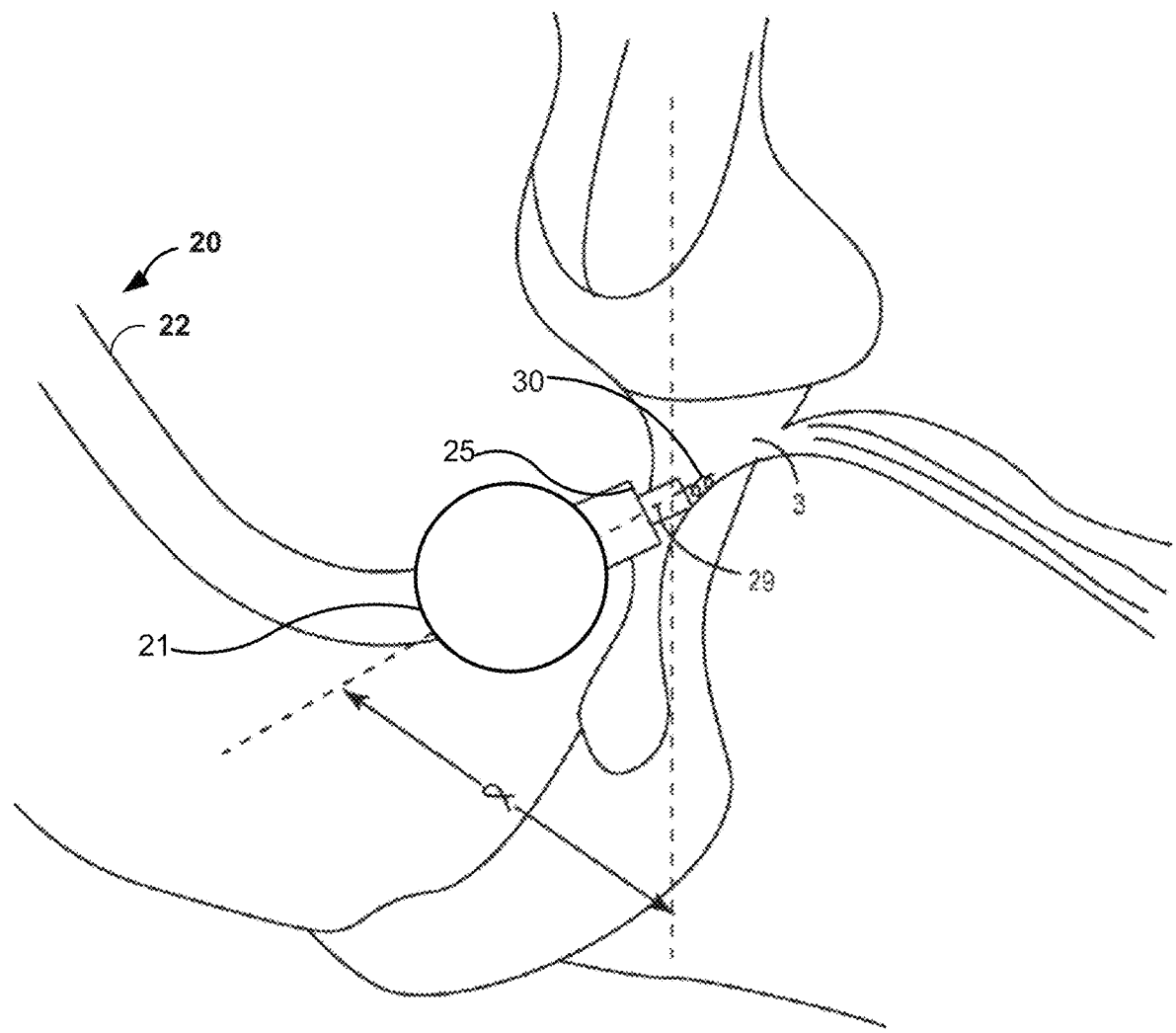
FIG. 1B is an enlarged view of the distal end of the catheter illustrated in FIG. 1A.

FIG. 1B is an enlarged view of a portion of the schematic diagram of FIG. 1A illustrating a medical electrical lead 29 that includes a fixation member 30 extending out of distal end 25 of catheter 20. In some examples, catheter 20 may include a delivery catheter configured to deliver medical electrical lead 29 or other medical devices, such as an IMD including a housing that contains circuitry configured for physiological sensing and/or generation of electrical stimulation. Medical electrical lead 29 is configured to provide physiological pacing of heart 14 via electrical pulse delivered to tissue at a selected location. Fixation member 30 may be configured to anchor medical electrical lead 29 to the tissue at the selected location. For example, during delivery of medical electrical lead 29, a clinician may control, via a lead body of medical electrical lead 29 controllable at or near a handle assembly of catheter 20, fixation member 30 to screw a helical-shaped fixation member 30 into the tissue at the selected location. Although illustrated as helical, in some examples, medical electrical lead 29 (or other medical device) may include additional or alternative fixation elements, including, but not limited to, one or more tines or one or more barbs. In some examples, echogenic member 21 may include an asymmetric shape configured to enable a clinician to determine an orientation of medical electrical lead 29 and/or fixation member 30 prior to or during deployment of fixation member 30 into tissue at a selected location.

Figure 2A:
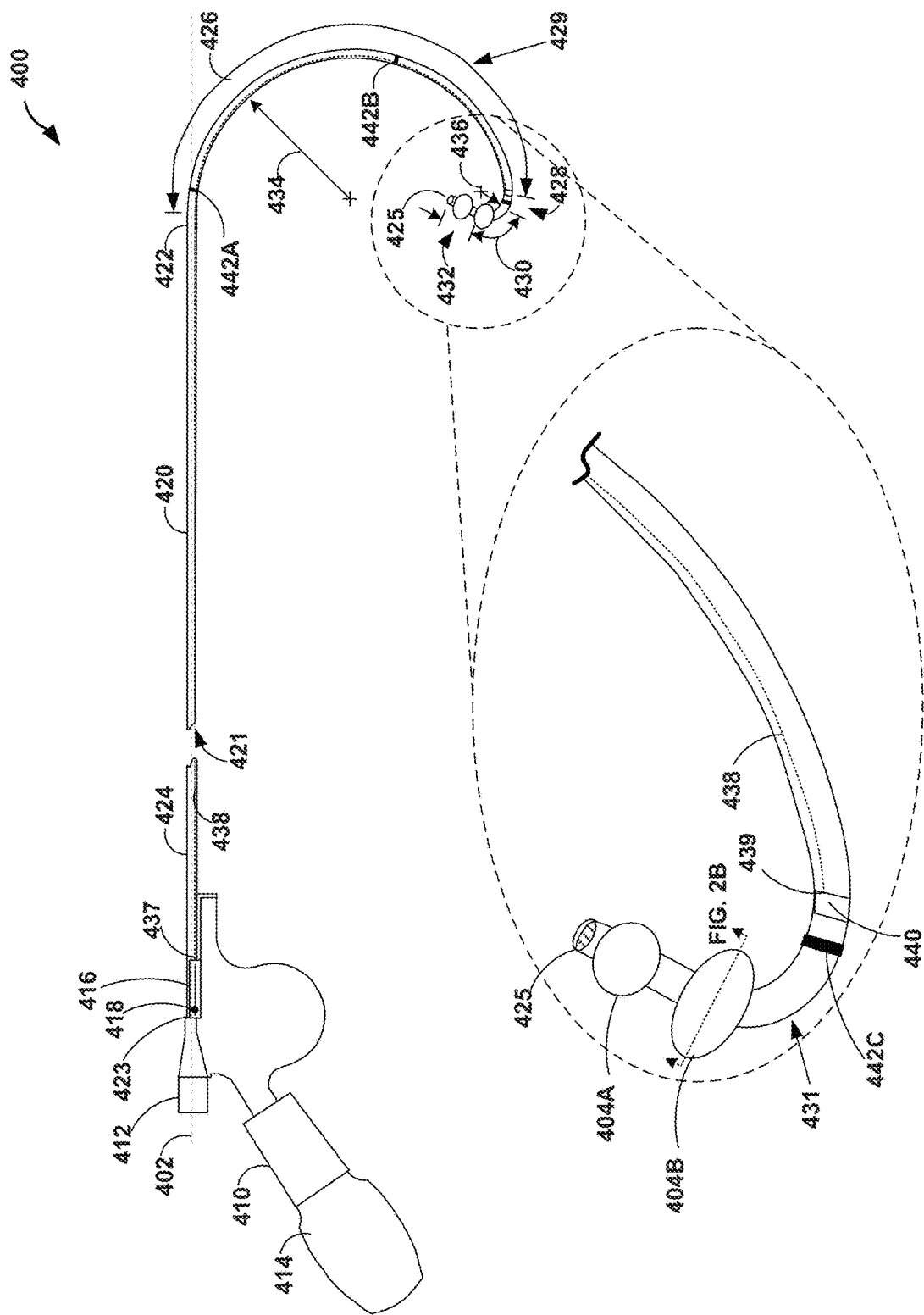
FIG. 2A is a conceptual diagram illustrating an example catheter that includes an elongated body having two echogenic members and a handle assembly.
Figure 2B:
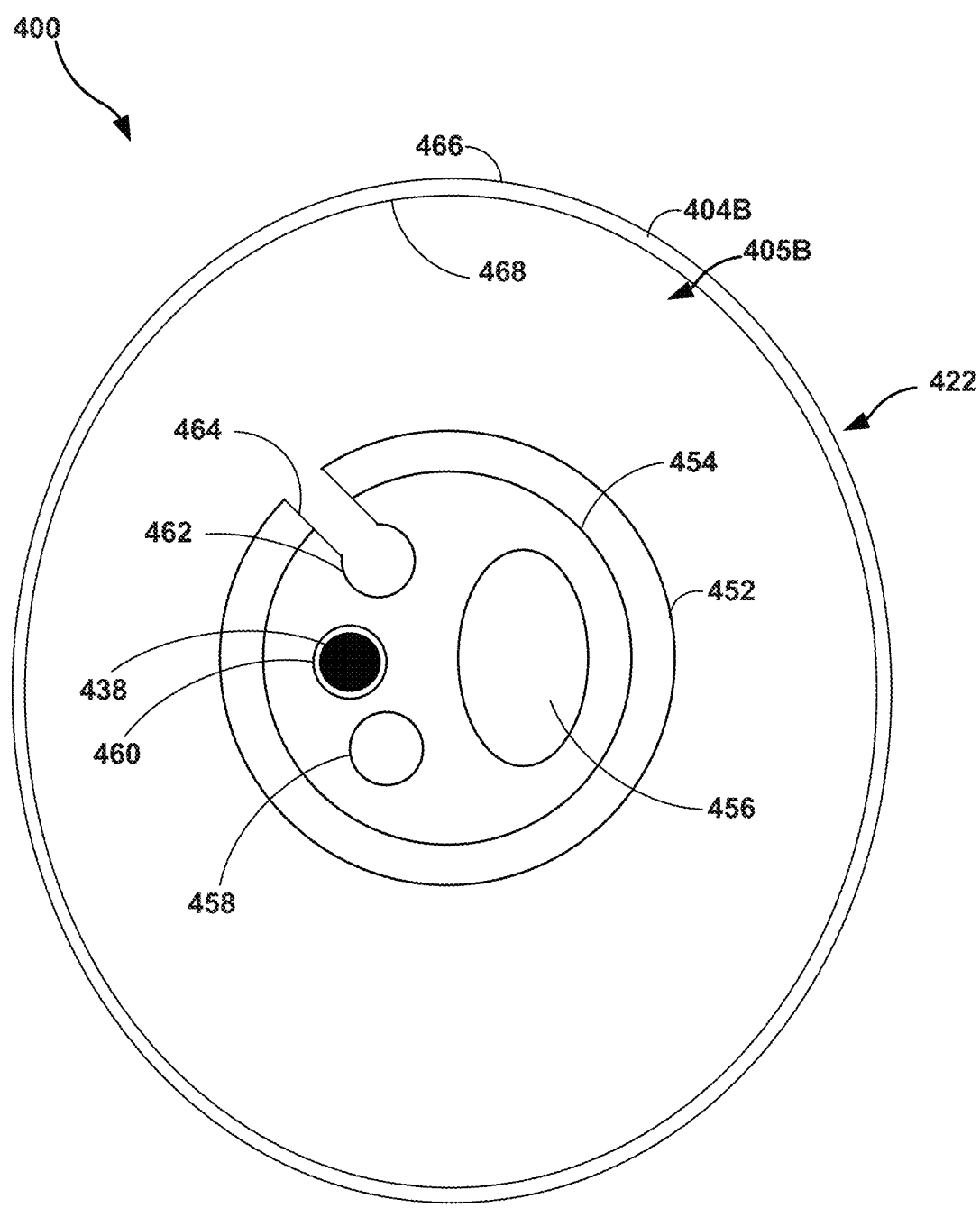
FIG. 2B is a conceptual diagram illustrating a cross-sectional view of the catheter illustrated in FIG. 2A.

In some examples, a catheter may include more than one echogenic member. FIGS. 2A and 2B are conceptual diagrams illustrating an example catheter 400 including a handle assembly 410, an elongate body 420, and echogenic members 404A and 404B (collectively, "echogenic members 404"). Catheter 400 may be the same as or substantially similar to catheter 20 discussed above in reference to FIGS. 1A and 1B, except for the differences described herein.

Elongate body 420 extends from a proximal end 423 to a distal end 425. Elongate body 420 may include any suitable length to reach the selected location of the heart from an access site, such as a femoral access site or a radial access site. In some examples, a length of elongate body may be in a range between about 30 centimeters (cm) and about 100 cm. Elongate body 420 defines a lumen 421 extending longitudinally within elongate body 420. Lumen 421 may be configured to receive an medical electrical lead or IMD. For example, lumen 421 may be sized to pass an medical electrical lead through an entire length of lumen 421. In some examples, elongate body 420 may include a plurality of lumens, each lumen extending along and/or parallel to longitudinal axis 402. In examples in which echogenic member 404 includes a balloon, one or more lumens may be configured to inflate and/or deflate echogenic member 404.

Elongate body 420 may include proximal portion 424 near proximal end 423 and distal portion 422 near distal end 425. Elongate body 420 has a flexibility allowing deflection of proximal portion 424 and/or distal portion 422 when elongate body 420 is maneuvered within the vasculature of a patient. Proximal portion 424 may be coupled to handle assembly 410 having a control member 416. Proximal portion 424 extends along longitudinal axis 402. In some examples, proximal portion 424 may include a stabilizing sheath that surrounds proximal portion 424 and is configured to transfer force, such as torque, at handle assembly 410 to distal portion 422.

In some examples, handle assembly 410 may include a hub 412, adjustable handle 414, and/or control member 416. Hub 412 may be configured to provide access to a lumen of elongate body 420. For example, hub 412 may provide access to a lumen fluidly coupled to echogenic members 404 that include inflatable balloons. In this way, a clinician may use a fluid to inflate and/or deflate echogenic member 404, for example, via a syringe. In some examples, handle assembly 410 may include a flushing assembly configured to couple to a syringe to, for example, purge air from lumens of catheter 400. Adjustable handle 414 may be configured to manipulate, e.g., rotate, the deflection of distal portion 422. Control member 416 may include one or more controls 418 that are coupled to one or more pull wires 438. One or more controls 418 may be manipulated to control a length of pull wire 438 extending through elongate body 420.

Echogenic members 404 are positioned on distal portion 422 of elongate body 402. Echogenic members 404 are configured to controllably expand from a collapsed configuration to an expanded configuration and diffusely scatter soundwaves, as discussed above. Echogenic member 404A is disposed near distal tip 425. For example, as discussed above, echogenic member 404A may be disposed proximal distal end 425 a distance within a range from about 0 mm to about 2 mm. Echogenic member 404B is proximal to echogenic member 404A. For example, echogenic member 404B may be space apart from echogenic member 404A a distance within a range from about 1 mm to about 30 mm, such as about 5 mm to about 25 mm or about 10 mm to about 20 mm. In some examples, echogenic members 404A and 404B may be directly adjacent. In examples in which echogenic members 404A and 404B are directly adjacent, the volume of echogenic members 404A and 404B that expands (e.g., a maximum diameter of the expanded configuration) may be separated a distance within a range from about 1 mm to about 30 mm, such as about 5 mm to about 25 mm or about 10 mm to about 20 mm. In some examples, a single echogenic member may include tow or more distinct expandable regions, such that the expandable regions define echogenic members 404A and 404B.

In some examples, echogenic members 404, spaced apart by a selected distance, may enable a clinician to determine an orientation and/or a trajectory of catheter 400 relative to surrounding soft tissue. For example, by visualizing both echogenic member 404 in the plane of an ultrasound, a clinician may determine that at least distal portion 422 including the echogenic members 404 is oriented in the plane. This enables determining that an orientation and/or trajectory of at least distal portion 422 is in the plane of the surrounding anatomy of the patient indicated by the ultrasound. Determining the orientation and/or trajectory of distal portion 422 may facilitate traversing valves of the heart or tunneling between chambers of the heart, such as from the right atrium to the left ventricle or from the right ventricle to the left ventricle. Compared to other medical imaging techniques having reduced soft tissue visibility, such as fluoroscopy, the use of echogenic members to determine an orientation and/or a trajectory of catheter 400 relative to a surrounding anatomy using ultrasound may improve clinician confidence and speed with respect to navigating the vasculature of a patient.

The size and shape of the first and second echogenic members may be similar or dissimilar. For example, as illustrated in FIG. 2A, echogenic member 404A may be smaller and more spherical compared to echogenic member 404B. This dissimilarity in size and/or shape may enable a clinician to distinguish between echogenic members 404A and 404B. Distinguishing between echogenic members 404A and 404B may enable determining an orientation and/or a trajectory of distal portion 422. In some examples, the distance between echogenic members 404 may be based on the size and/or shape of echogenic members 404. For example, an ultrasound image showing the total diameter of echogenic member 404A may indicate that echogenic member 404A is centered in the plane of the surrounding anatomy indicated by the ultrasound image. When the ultrasound image shows a portion of echogenic member 404B less than the total diameter of echogenic member 404B, the clinician may determine that an orientation and/or trajectory of catheter 400 is either above or below the plane of the ultrasound image. In some examples, smaller echogenic members may enhance resolution of the alignment with the ultrasound plane compared to larger echogenic members. In some examples, larger echogenic members may be easier to track compared to smaller echogenic members. In this way, the size and spacing of echogenic member 404 may be selected to improve visualization of catheter 400 (e.g., distal portion 422) using ultrasound which may improve determination of a trajectory and an orientation of distal portion 422 relative to surrounding tissue compared to other medical imaging techniques, such as fluoroscopy.

Although described as including two echogenic members 404, in some examples, catheter 400 may include three or more echogenic members disposed on distal portion 422 of catheter 400 to enable a clinician to determine a position, orientation, and/or trajectory of selected portions of catheter 400, including, for example, distal end 425, preformed curves 430, or articulating segment 426. For example, distal portion 422 may include an articulating segment 426 and a preformed curve segment 430 distal articulating segment 426. In this way, a shape of distal portion 422 may be controllable. For example, pull wire 438, e.g., by actuation of control member 416, may be configured to controllably bend articulating segment 426 in a first curve 429 in a first geometric plane. In some examples, the amount of actuation of control member 416 may control the degree of curvature of articulating segment 426. For example, a degree of curvature of articulating segment 426 may be controlled in a range between about 0 degrees to about 240 degree, such as between about 45 degrees and about 180 degrees or between about 85 degrees and about 100 degrees. In some examples, a length of articulating segment 426 defining first curve 429 may be within a range from about 5 cm to about 20 cm, such as from about 12 cm to about 15 cm. In some examples, a radius 434 of first curve 429, when articulated, may be within a range between about 5 mm and about 60 mm, such as between about 10 mm and about 30 mm or between about 15 mm and about 20 mm. By controlling the degree of curvature, articulating segment 426 may enable first curve 429 to be adjusted to accommodate a variation in the position of a selected location or a difference in size of a dilated heart compared to an average sized heart.

Pull wire 438 may enable control of the degree of curvature of articulating segment 426 from handle assembly 410. For example, a proximal end 437 of pull wire 438 may be coupled to control member 416. Pull wire 438 may extend from control member 416 to a distal end 439 of pull wire 438 anchored to elongate body 420 distal to articulating segment 426. For example, distal end 439 may be anchored to elongate body 420 using a pull band 440. Pull band 440 may include any suitable structure configured to anchor a distal end 439 of pull wire 438 to elongate body 420 distal articulating segment 426. In some examples, pull band 440 may include a radiopaque marker, gold, platinum iridium, other noble metals or alloys thereof, stainless steel, other materials configured to withstand deflection force from actuating pull wire 438 which may include sputtered noble metals, or combinations thereof. In some examples, pull wire 438 includes a single pull wire. In other example, pull wire 438 may include a plurality of pull wires. In examples in which pull wire 438 include a plurality of pull wires, each pull wire of the plurality of pull wires may be configured to control a deflection of distal portion 422 in one or more directions. Pull wire 438 may include any suitable material and construction. In some examples, pull wire 438 may have a diameter of approximately 0.009 inch (0.23 mm) and may be formed from medical grade 304 stainless steel. In some examples, pull wire 438 may include a coating, e.g., a fluoropolymer, such as polytetrafluoroethylene (PTFE). By anchoring distal end 439 of pull wire 438, actuation of control member 416 in a proximal direction, e.g., to shorten a length of pull wire 438 extending through elongate body, may result in a controllable bending of articulating segment 426 in first geometric plane P1. Actuation of control member 416 in a distal direction, e.g., to lengthen a length of pull wire 438, may result in a controllable return of articulating segment 426 to a resting state, e.g., unbent or less bent configuration.

In some examples, a shape of distal portion 422 may include a preformed curve. For example, preformed curve segment 430 defines a second curve 431 in a second geometric plane. The second geometric plane may be similar or different from the first geometric plane. For example, first geometric plane and second geometric plane may be offset by an offset angle. In some examples, the offset angle, e.g., the angle of first geometric plane relative to second geometric plane, may be within a range from about 10 degrees to about 80 degrees, such as about 30 degrees to about 60 degrees or about 40 degree to about 50 degrees.

In some examples, preformed curve segment 430 may be sufficiently flexible to deform into a substantially straight configuration when passed through the vasculature of a patient. Preformed curve segment 430 may be sufficiently resilient to regain the preformed shape of second curve 431 when positioned in the heart of the patient. In some examples, second curve 431 of preformed curve segment 430 may be formed by, for example, heat setting. In some examples, a degree of curvature of preformed curve segment 430 may be in a range between about 10 degrees to about 180 degree, such as between about 30 degrees and about 140 degrees. In some examples, a length of preformed curve segment 430 defining second curve 431 is within a range between about 6 cm and about 10 cm, such as between about 1 cm and about 5 cm or between about 1 cm and about 2 cm. In some examples, a radius 436 of second curve 431 is within a range between about 1 mm and about 20 mm, such as between about 2 mm and about 10 mm. The degree of curvature of preformed curve segment 430 may enable the distal end 425 to be oriented substantially normal to tissue at the selected location.

In some examples, distal portion 422 may include one or more substantially straight portions. For example, elongate body 420 may include substantially straight portion 428 distal articulating segment 426 and proximal preformed curve segment 430, and/or substantially straight portion 432 distal to preformed curve segment 430 and including distal end 425. In some examples, a length of substantially straight portion 428 and/or 432 may be in a range between about 1 mm and about 15 mm, such as between about 0.5 mm and about 9 mm. In some examples, echogenic member 404 may be disposed on one or more of substantially straight portions 428 or 432.

In some examples, distal portion 422 may include at least one radiopaque marker, such as at least one of radiopaque markers 442A, 442B, and/or 442C (collectively, radiopaque markers 442). Radiopaque markers 442 may include a gold foil, with an adhesive backing, which is sandwiched between layers of distal portion 422, such as any layer of distal portion 422 discussed below in reference to FIG. 2B. In some examples, distal portion 422 may include a first radiopaque marker, e.g., radiopaque marker 442A and/or 442B, on articulating segment 426 and a second radiopaque marker, e.g., radiopaque marker 442C, distal to articulating segment 426. In some examples, the second radiopaque marker, e.g., radiopaque marker 442C, may be at least one of on or distal to the preformed curve segment. In some examples, radiopaque markers 422 may be disposed on or directly adjacent to echogenic member 404. In this way, a position of echogenic members 404 may be determined by both ultrasound and fluoroscopy. By positioning radiopaque markers 442 on articulating segment 426 and distal to articulating segment 426, such as at least one of on or distal to the preformed curve segment, and/or on or adjacent to echogenic member 404 a three-dimensional position, orientation, and/or trajectory of distal portion 422 may be determined, e.g., observable by a clinician via fluoroscopy.

Articulating segment 426 and preformed curve segment 430 may include any suitable material and construction to achieve flexibility, pushability, and torque transfer that facilitates maneuverability of catheter 400 to a selected location within the heart of the patient. For example, articulating segment 426 and preformed curve segment 430 may include one or more coaxial layers of polyether block amide, polyurethane, or silicone rubber, or composites thereof.

FIG. 2B is a conceptual diagram illustrating a cross-sectional view of catheter 400 at echogenic member 404B. In some examples, distal portion 422 may be defined by exterior layer 452 and inner assembly 454. In some examples, exterior layer 452 may include one or more rigid materials, such as, for example, a coiled or braided metal coil or mesh, such as stainless steel or nitinol, coated in one or more flexible, biocompatible material such as, for example, silicone or polyurethane. In some examples, inner assembly 454 may include a lubricious polymer, such as PTFE. Inner assembly 454 may include a plurality of lumens, such as one, relatively large lumen 456, and three, relatively small lumens 458, 460, and 462. Lumens 456, 458, 460, and 462 may be fluidly coupled with a distal end 425 of the catheter 400 and/or a proximal port of handle assembly 410 (FIG. 2A). Lumen 456 may be sized to enable a medical device, such as a medical electrical lead, to pass therethrough. Pull wire 438 may extend within lumen 460. Lumen 462 may be fluidically coupled to lumen 405B via channel 464. In this way, a clinician may inject fluid, e.g., via a syringe, into lumen 462 to inflate echogenic member 404B. Likewise, a clinician may controllably withdraw fluid from lumen 405B via lumen 462. Similarly, lumen 458 may be fluidically coupled to a lumen (not shown) defined by echogenic member 404A. In other examples, inner assembly 454 may include a tube having any number of lumens or a single lumen.

Echogenic member 404A may define an exterior surface 466 and an interior surface 468. In some examples, one or both of exterior surface 466 and interior surface 468 may be coated with an echogenic coating, as described above. In some examples, the sidewall defining echogenic member 404B may be impregnated with an echogenic material. Additionally, or alternatively, a fluid configured to inflate echogenic member 404A may include an echogenic material.

Figure 3A:
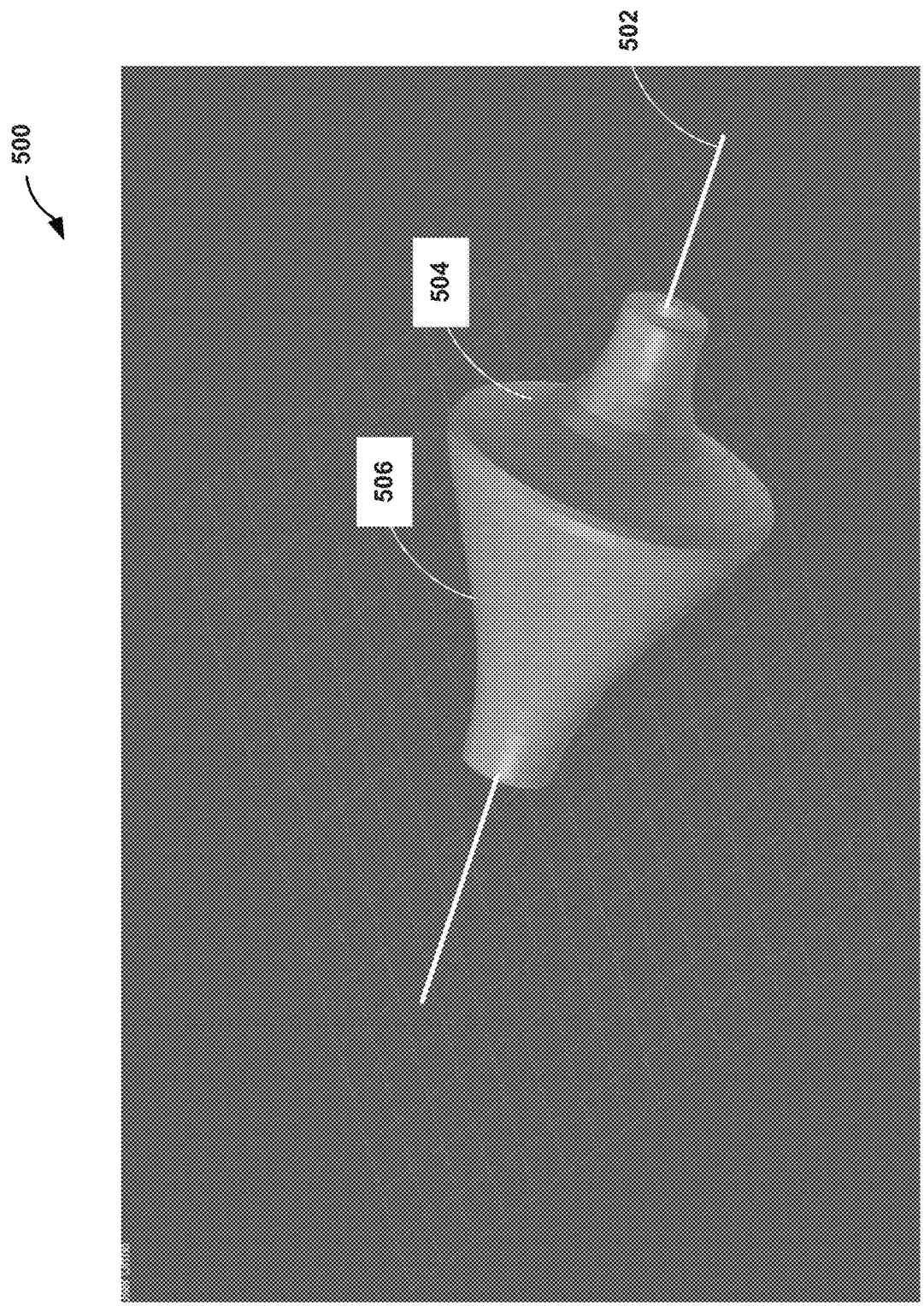
FIGS. 3A-3D are a conceptual diagram and cross-sectional views of an example echogenic member having a tapered shape.
Figure 3D:
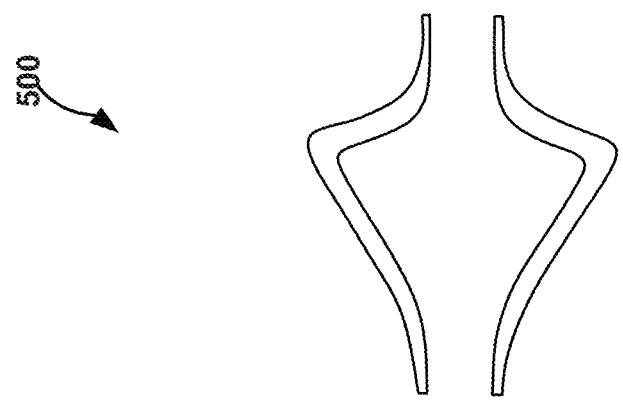
Figure 3C:
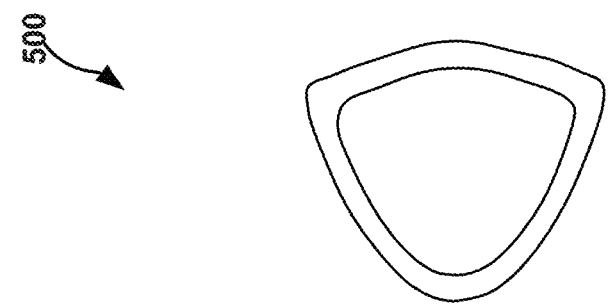
Figure 3B:
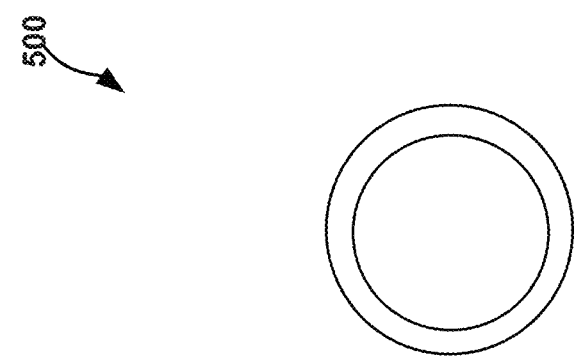

As discussed above, an echogenic member may include any suitable shape. FIG. 3A-3D are conceptual diagrams illustrating an example echogenic member 500 having a tapered shape. Echogenic member 500 extends along a principal axis 502, which may be configured to align with the longitudinal axis of a catheter, e.g., longitudinal axis 402, when positioned on a catheter. The tapered shape includes two half cones 504 and 506. Half cones 504 and 506 taper toward longitudinal axis 502 at different angles. In some examples, the shape of half cones 504 and 506 may enable a clinician to determine an orientation of echogenic member 500. For example, as illustrated in FIG. 3B, an ultrasound image of echogenic member 500 in a plane perpendicular to principal axis 502 may resemble a circle or concentric circles. As illustrated in FIG. 3C, an ultrasound image of echogenic member 500 in a plane off-axis relative to principal plane 502 may resemble an irregular shape. As illustrated in FIG. 3D, an ultrasound image of echogenic member 500 in a plane longitudinal to principal axis 502 may resemble a longitudinal cross section of echogenic member 500.

Figure 4:
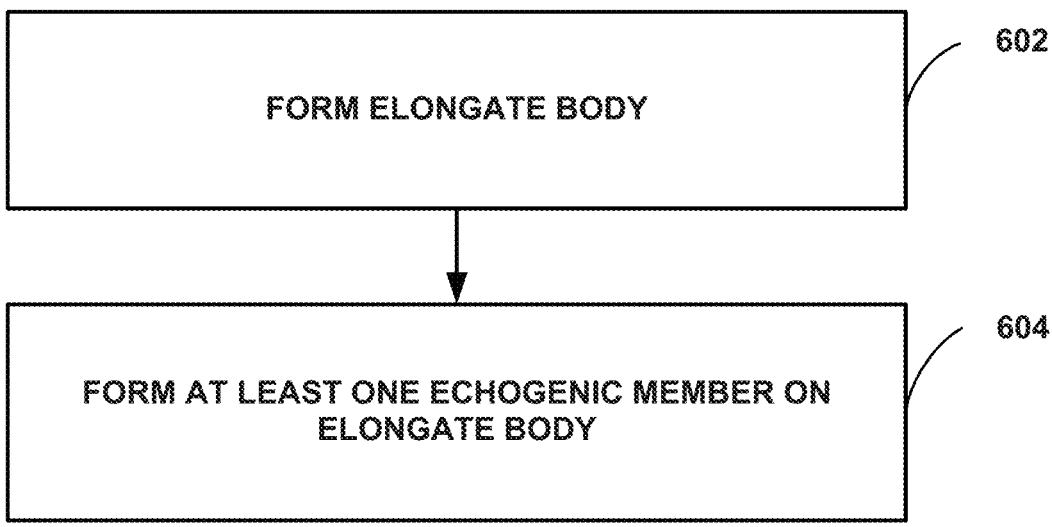
FIG. 4 is a flow diagram illustrating an example method for manufacturing an example catheter.

The catheters described herein may be assembled by any suitable technique. FIG. 4 is a flow diagram illustrating an example method for assembling an example catheter including an echogenic member. The catheter may be the same as or substantially similar to catheters 20 and/or 400 discussed above with respect to FIGS. 1A-2B. Although FIG. 4 is described with respect to catheter 400, in other examples, the method of FIG. 4 may be used to assemble other catheters having echogenic members.

The technique illustrated in FIG. 4 includes forming elongate body 420 (602). As discussed above, elongate body 420 may extend from proximal end 423 to distal end 425 and defining lumen 421 extending longitudinally within elongate body 420. Lumen 421 may be configured to receive a medical electrical lead that includes at least one electrode and/or an IMD. Elongate body 420 may include proximal portion 424 and distal portion 422. Proximal portion 424 may extend along longitudinal axis 402 and may be configured to couple to handle assembly 410. Distal portion 422 may include at least one echogenic member 404 and, optionally, an articulating segment 426 and/or a preformed curve segment 430.

Elongate body 420 may be formed by any suitable technique, such as, for example, extrusion of one or more polymers to form inner assembly 454 and deposition of one or more polymer layers on the elongate tube. Two or more elongate tubes may be molded or otherwise adhered together to define inner assembly 454. In some examples, forming elongate body 420 may include winding or braiding one or more metal wires onto a mandrel (or inner assembly 454) to form a reinforcement structure. In some examples, one or more polymer layers may be deposited on an internal surface and/or external surface of the reinforcement structure to define exterior layer 452.

In some examples, forming elongate body 420 may include forming proximal portion 424, forming distal portion 422, and attaching proximal portion 424 to distal portion 422. Attaching proximal portion 424 to distal portion 422 may include, for example, adhering proximal portion 424 to distal portion 422 using a suitable adhesive or welding (e.g., thermal welding or ultrasonic welding) proximal portion 424 to distal portion 422.

In some examples, forming distal portion 422 may include heat setting (e.g., thermoforming) at least a portion of distal portion 422 to form preformed curve segment 430. In some examples, forming distal portion 422 may include at least forming a relatively soft section extending longitudinally along a first length of articulating segment 526 and forming, on at least a portion of a surface of the relatively soft section, a relatively stiff section extending longitudinally along a second length of articulating segment 526.

In some examples, the technique may include anchoring distal end 439 of pull wire 438 to elongate body 420. As discussed above, pull wire 438 may extend from control member 416 of handle assembly 410 to distal end 439 such that pull wire 438, by actuation of control member 416, may be configured to controllably bend articulating segment 426 in a first curve in first geometric plane P1. In some examples, anchoring distal end 439 to elongate body 420 may include adhering or otherwise affixing distal end 439 to a portion of elongate body 420, such as a portion of lumen 524.

The technique illustrated in FIG. 4 also includes forming on elongate body 420 at least one echogenic member 404 (604). In some examples, a tube defining echogenic member 404 may be formed by, for example, extrusion of a polymer. In some examples, a reinforcing structure such as a metal coil or mesh may be embedded in or disposed directly on the polymer defining echogenic member 404. Echogenic member 404 may be fixed to a selected portion of elongate body 420 by, for example, an adhesive, thermowelding, or ultrasonic welding. In some examples, the technique may include applying an echogenic coating to echogenic member 404. For example, echogenic member 404 may be dip-coated in an echogenic coating or an echogenic coating may be injected into echogenic member after fixing echogenic member 404 to elongate body 420.

In some examples, the technique may include positioning at least one radiopaque marker on distal portion 422. In some examples, positioning at least one radiopaque marker may include adhering a radiopaque material, such as gold foil, between layers of distal portion 422, such as between inner assembly 454 and exterior layer 452.

Figure 5:
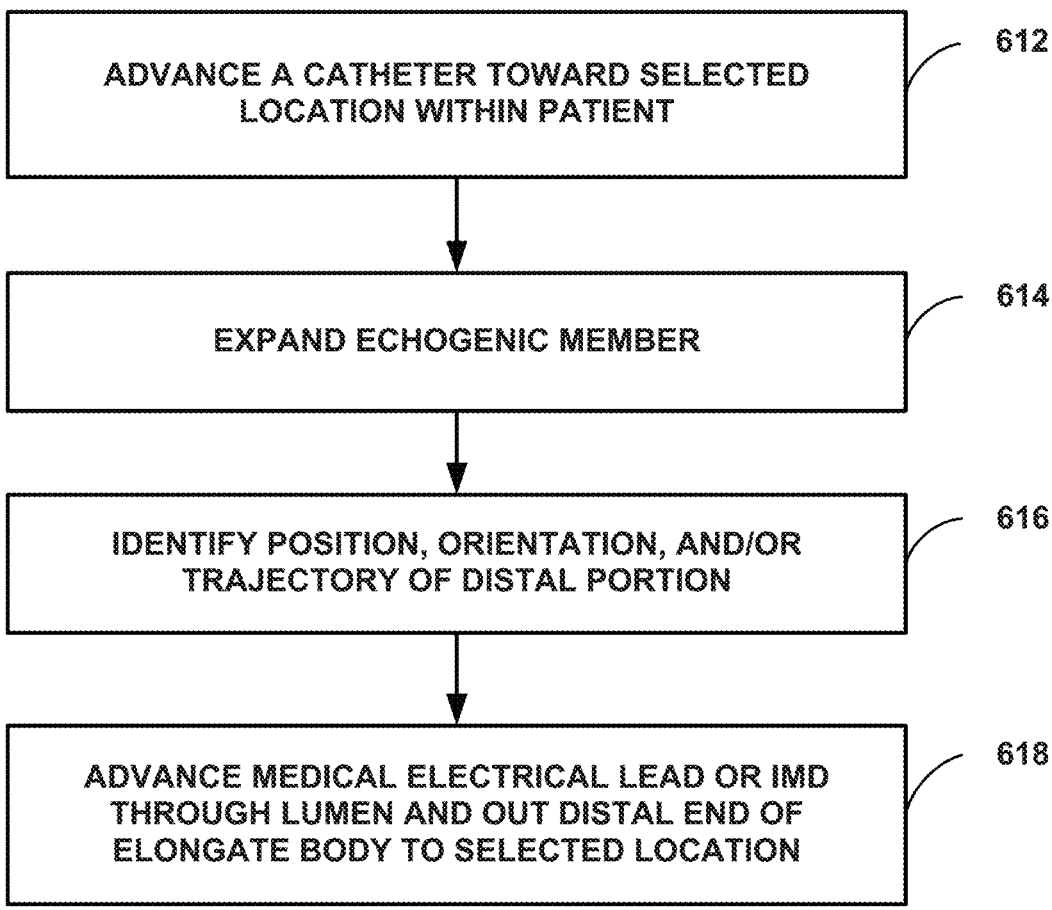
FIG. 5 is a flow diagram illustrating an example method of delivering an example catheter to a selected location using an example catheter.

The catheters described herein may be used to deliver a medical electrical lead or IMD using any suitable technique. FIG. 5 is a flow diagram illustrating an example method of delivering a medical electrical lead to a selected location using an example catheter including an echogenic member. The catheter may be the same as or substantially similar to catheters 20 and/or 400 discussed above with respect to FIGS. 1A-2B. Although FIG. 5 is described with respect to catheter 400, in other examples, the method of FIG. 5 may be used with other catheters having at least one echogenic member.

The technique illustrated in FIG. 5 includes advancing catheter 400 toward a selected location within a patient (612). In some examples, after advancing catheter 400 toward the selected location, the technique may include actuating control member 416, e.g., via one or more controls 418, to cause pull wire 438 to controllably bend articulating segment 426 into first curve 429.

The technique illustrated in FIG. 5 also includes expanding echogenic member 404 from a collapsed configuration to an expanded configuration (614). At least when in the expanded configuration, echogenic member 404 is configured to diffusely scatter a soundwave such that echogenic member 404 is identifiable using an ultrasound imaging device. In some examples, expanding echogenic member 404 may include injecting a fluid, such as saline or an echogenic fluid, into echogenic member 404 via one or more lumens of catheter 400. In some examples, expanding echogenic member 404 may include actuating control member 416, e.g., via one or more controls 418, to cause pull wire 438 to expand echogenic member 404.

The technique illustrated in FIG. 5 also includes identifying at least one of a position, an orientation, or a trajectory of the distal portion of the catheter relative to the selected location based on a soundwave reflected by the echogenic member (616). In some examples, identifying (616) may include imaging, by an ultrasound imaging device, the at least one echogenic member 404. For example, imaging may include capturing a plurality of images of the at least one echogenic member 404 and surrounding anatomy. Each image of the plurality of images may include different angles of an ultrasound transceiver relative to the catheter 400 and/or the surrounding anatomy. In some examples, identifying (616) may include determining, based on the ultrasound image, a position, an orientation, and/or a trajectory of distal portion 422 (e.g., distal end 425) relative to the surrounding anatomy. For example, determining a position, an orientation, and/or a trajectory of distal portion 422 may include comparing a size and/or a shape of echogenic member 404 to a known size and/or shape of one or more cross sectional geometries of echogenic member 404. In some examples, determining a position, an orientation, and/or a trajectory of distal portion 422 may include comparing a size and/or a shape of a first echogenic member 404A to a size and/or a shape of a second echogenic member 404B. In some examples, after determining the position, the orientation, and/or the trajectory of distal portion 422, the technique may include further advancing, repositioning, or reorienting distal portion 422, and repeating imaging the at least one echogenic member 404.

The technique illustrated in FIG. 6 also includes, after identifying the selected location, advancing medical electrical lead 29 or an IMD through lumen 421 and out distal end 425 of elongate body 420 to the selected location (618). For example, the technique may include advancing medical electrical lead 29 out of distal end 425 of catheter 400 and controlling fixation member 30, e.g., via a lead body of medical electrical lead 29 controllable at or near a handle assembly of catheter 20, to screw fixation member 30 into the tissue at the selected location.

EXAMPLES

Figure 6A:
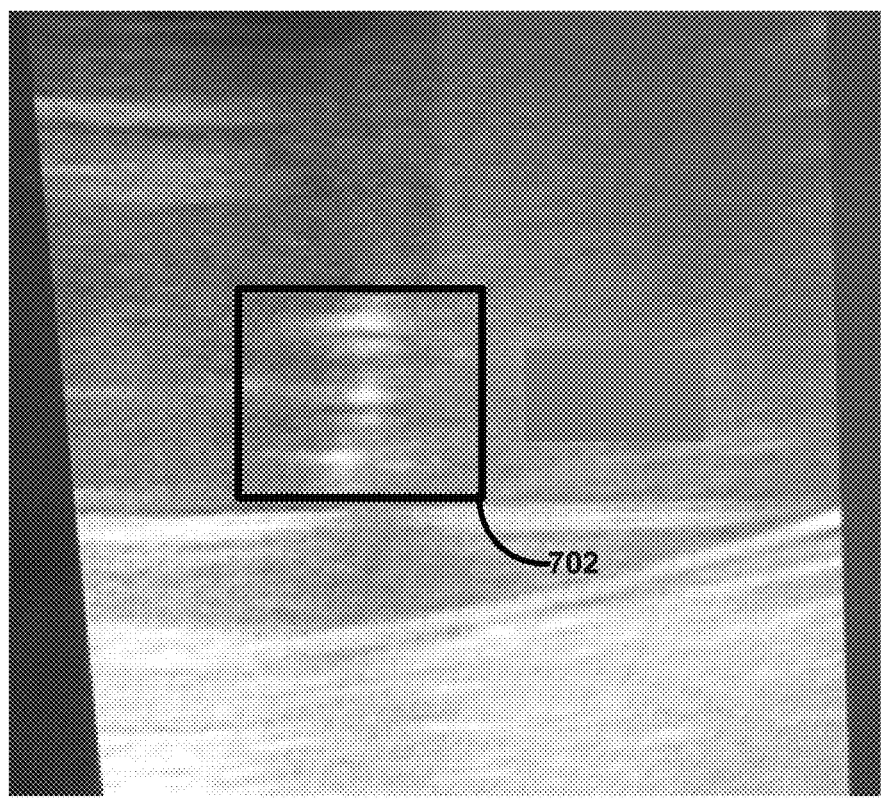
FIGS. 6A and 6B are photographs illustrating an example ultrasound image of an expandable member of a catheter positioned within a heart of a patient.
Figure 6B:
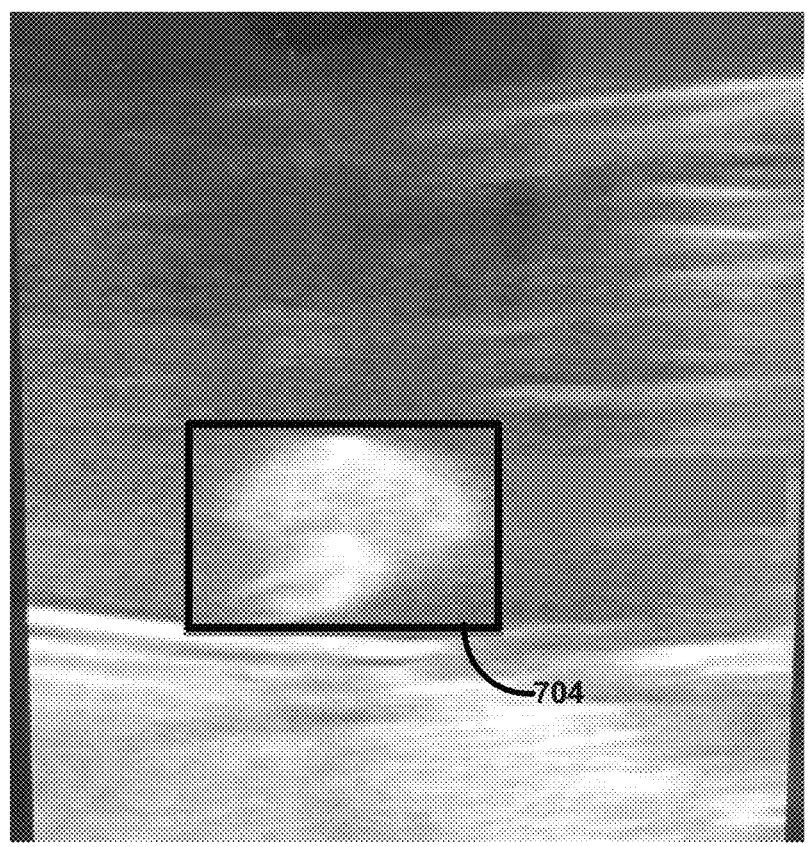

FIGS. 6A and 6B are photographs illustrating an example ultrasound image of an expandable member of a catheter positioned within a heart of a patient. As illustrated in FIG. 6A, a non-echogenic expandable member (e.g., not having an echogenic coating) is positioned within the region indicated by box 702. The non-echogenic expandable member is obscured in the ultrasound image. Thus, it may be difficult for a clinician observing the non-echogenic expandable member using an ultrasound imaging device to distinguish the non-echogenic expandable member from the surrounding anatomy. As illustrated in FIG. 6B, an expandable echogenic member (e.g., having an echogenic coating) is positioned within the region indicated by box 704. The expandable echogenic member is clearly visible in the ultrasound image. Thus, a clinician observing the expandable echogenic member using an ultrasound imaging device may readily distinguish the expandable echogenic member from the surrounding anatomy. Similarly, an expandable member filled with an echogenic fluid may be visible and distinguishable from the surrounding anatomy. In this way, an echogenic coating or an echogenic fluid may be used to improve the sound scattering produced by an expandable member to enable ultrasound imaging of the expandable member.

Figure 7A:
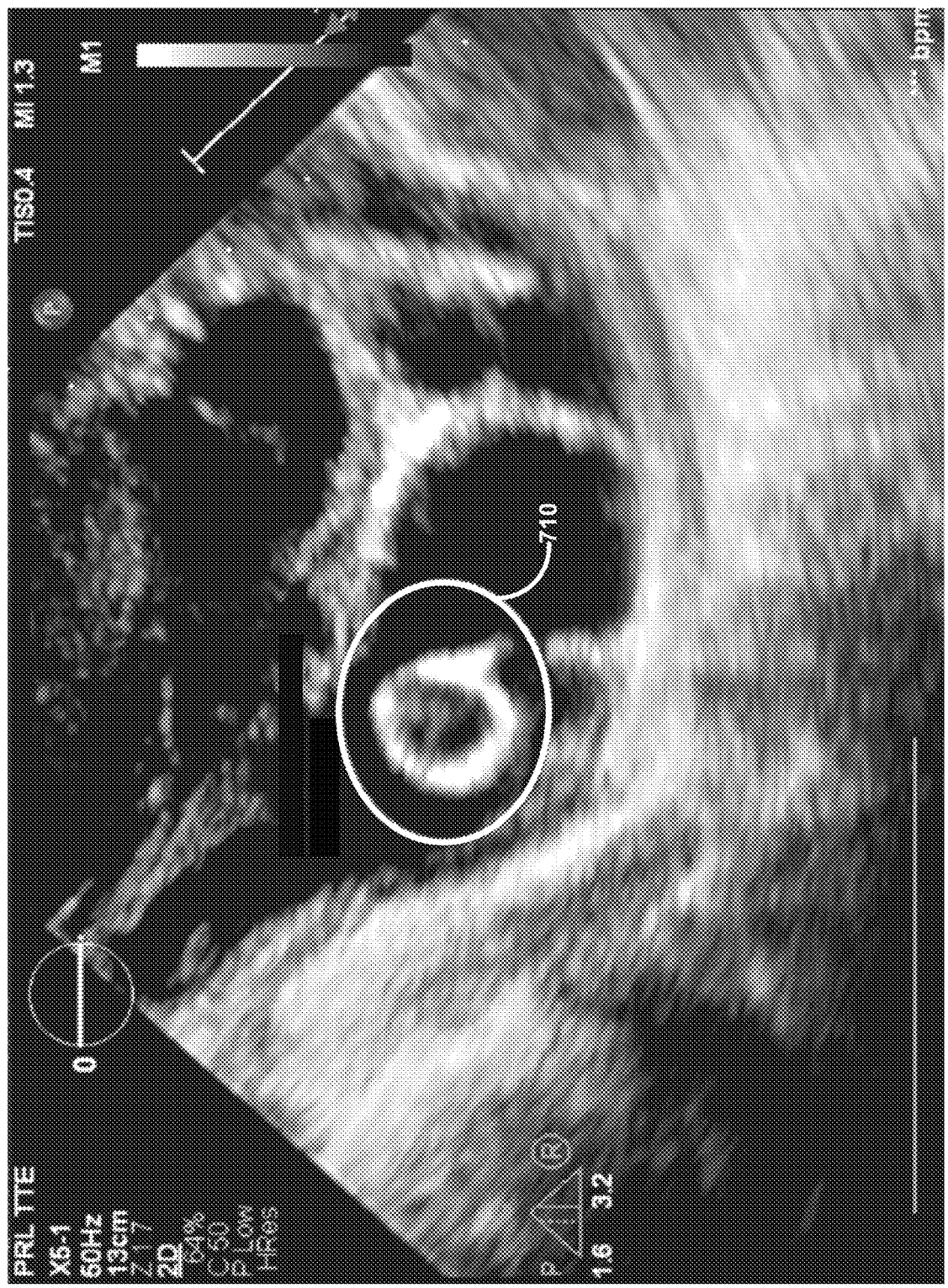
FIGS. 7A and 7B are photographs illustrating an example ultrasound image of an expanded echogenic member of a catheter positioned within a heart of a patient.
Figure 7B:
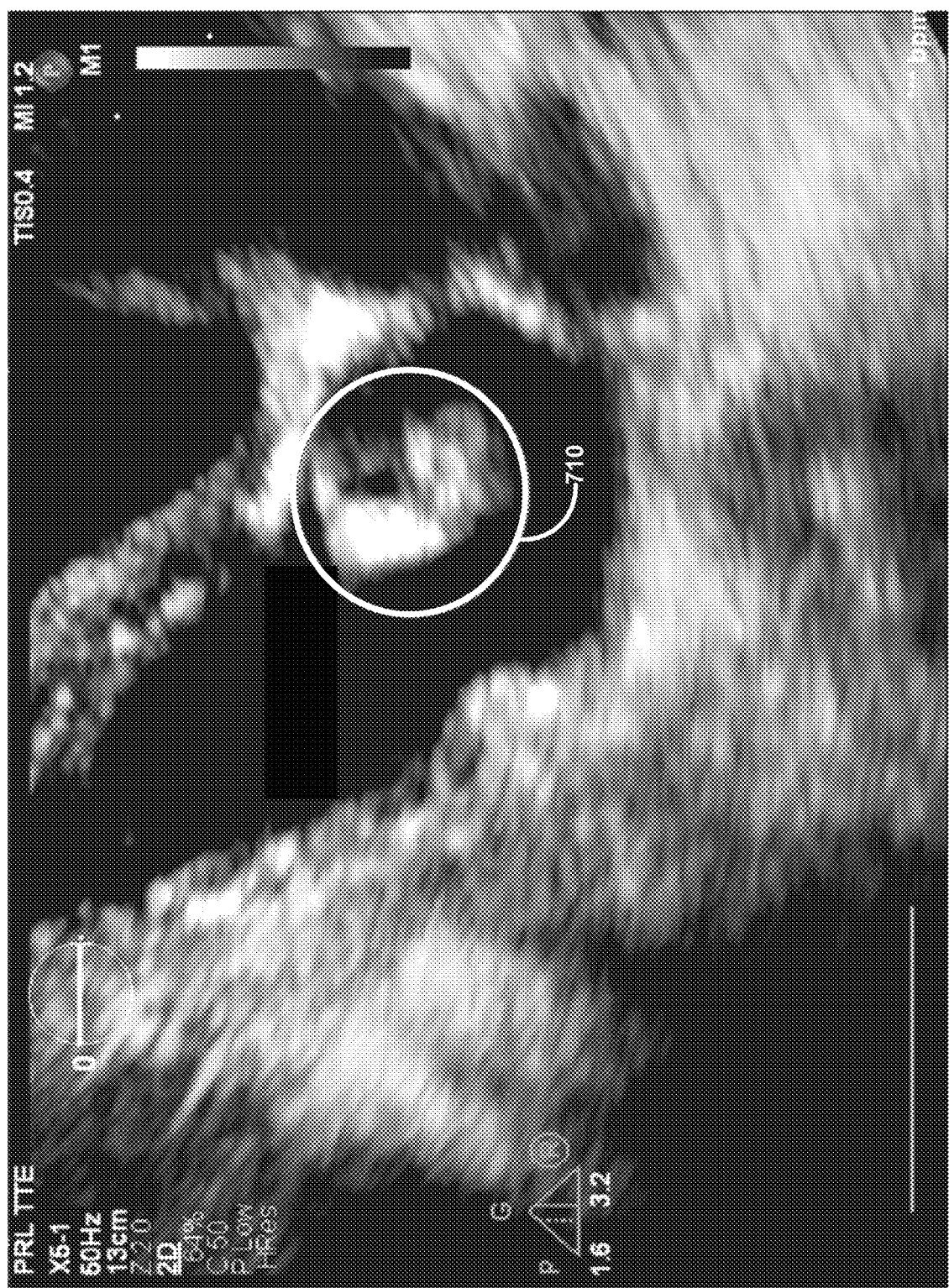

FIGS. 7A and 7B are photographs illustrating an example ultrasound image of an expanded echogenic member of a catheter positioned within a heart of a patient. As illustrated in FIGS. 7A and 7B, the echogenic member positioned within the region indicated by circle 710 is visible and distinguishable from the surrounding anatomy.

Figure 8A:
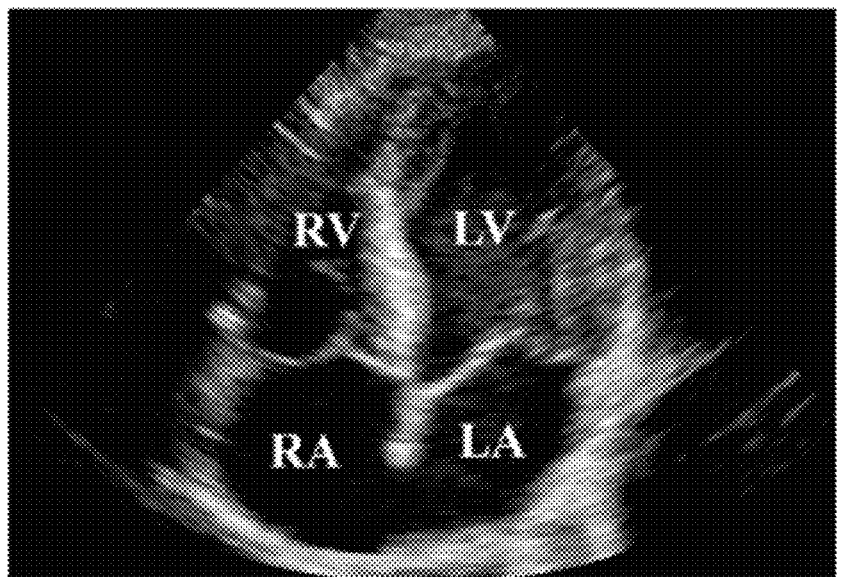
FIGS. 8A-8C are photographs illustrating example ultrasound images of a catheter positioned within a heart of a patient.
Figure 8B:
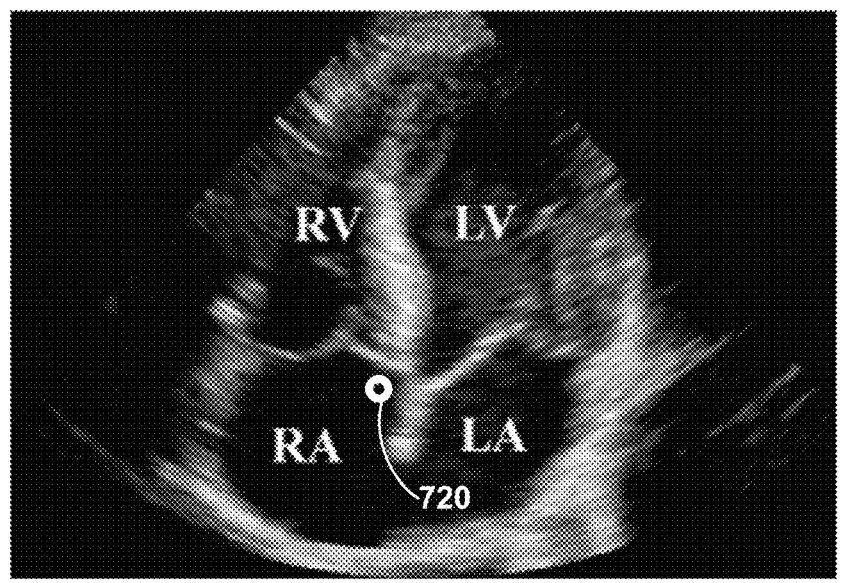
Figure 8C:
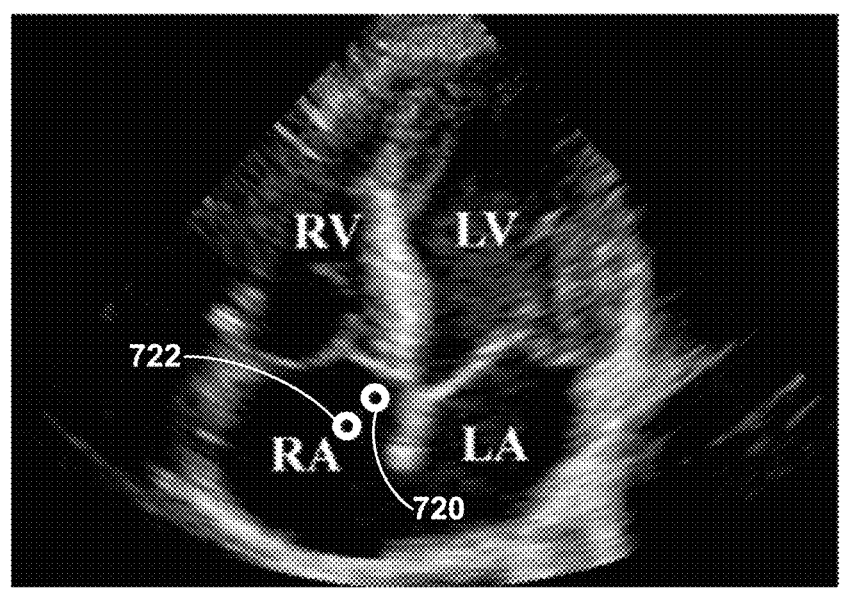

FIGS. 8A-8C are photographs illustrating example ultrasound image of an example catheter positioned within a heart of a patient. The catheter includes two echogenic members 720 and 722. In the example of FIGS. 8A-8C, echogenic members 720 and 722 are positioned near a distal end of the catheter, e.g., as described in reference to FIG. 2A. In other example, echogenic members may be disposed at other positions on the catheter. The ultrasound transducer is positioned from an apical view such that the plane of the ultrasound image traverses the four chambers of the heart. As illustrated in FIG. 8A, when the 2D plane of the ultrasound image is not aligned with echogenic members 720 and 722, e.g., not aligned with the position, orientation, or trajectory of the catheter, neither echogenic member is visible. When the catheter is re-oriented with respect to the 2D plane of the ultrasound image (illustrated here as stationary) echogenic member 720 is visible, as illustrated in FIG. 8B. For example, the catheter may extend through the 2D plane of the ultrasound image such that only echogenic member 720 is visible. In other words, the catheter is not aligned with the 2D plane of the ultrasound image. As illustrated in FIG. 8C, when the catheter is aligned with the 2D plane of the ultrasound image, both echogenic members 720 and 722 are visible. In other words, the catheter is oriented in the plane represented by the ultrasound image, and its trajectory (e.g., if advanced in a distal direction) is in the plane represented by the ultrasound image. For example, echogenic members 720 and 722 indicate that the catheter is aligned to tunnel from the right atrium (RA) to the left ventricle (LV). In this way, echogenic members 720 and 722 may be used to facilitate guiding a catheter through a heart of a patient by enabling a clinician to determine a position, orientation, and/or trajectory of a catheter relative to the surrounding anatomy of the patient.

The following clauses illustrate example subject matter described herein.

Clause 1. A catheter comprising: an elongate body extending along a longitudinal axis from a proximal end to a distal end and defining a lumen extending longitudinally within the elongate body, the elongate body comprising a proximal portion and a distal portion; and an echogenic member positioned on the distal portion of the elongate body, wherein the echogenic member is configured to controllably expand from a collapsed configuration to an expanded configuration, and wherein the echogenic member is configured to diffusely scatter a soundwave.

Clause 2. The catheter of Clause 1, wherein the echogenic member comprises balloon inflatable from the collapsed configuration to the expanded configuration and deflatable from the expanded configuration to the collapsed configuration.

Clause 3. The catheter of Clause 1, wherein the echogenic member comprises at least one of a self-expanding member or controllably expanding member.

Clause 4. The catheter of any one of Clauses 1 through 3, wherein, when in the collapsed configuration, a diameter of the echogenic member is less than about 9.5 millimeters (mm).

Clause 5. The catheter of any one of Clauses 1 through 4, wherein, when in the expanded configuration, a diameter of the echogenic member is within a range between about 1 mm and about 30 mm.

Clause 6. The catheter of any one of Clauses 1 through 5, wherein the echogenic member is positioned between about 0 mm and about 5 mm from the distal end of the elongate body.

Clause 7. The catheter of any one of Clauses 1 through 6, wherein a shape of the echogenic member is a shape selected from the group including a sphere, an ellipse, and a frustum.

Clause 8. The catheter of any one of Clauses 1 through 7, wherein the echogenic member comprises a distal end and a proximal end, each coupled to an external surface of the elongate member, wherein the echogenic member is tapered toward the longitudinal axis at at least one of the distal end or the proximal end of the echogenic member.

Clause 9. The catheter of any one of Clauses 1 through 8, wherein the echogenic member comprises an echogenic coating.

Clause 10. The catheter of Clause 10, wherein the echogenic coating comprises an echogenic polymer.

Clause 11. The catheter of Clause 10, wherein the echogenic member is configured to be inflated with an echogenic fluid.

Clause 12. The catheter of any one of Clauses 1 through 11, further comprising a radiopaque marker on the distal portion of the elongate body.

Clause 13. The catheter of any one of Clauses 1 through 12, wherein the echogenic member comprises a first echogenic member, wherein the catheter further comprises a second echogenic member proximal to the first echogenic member on the distal portion of the elongate body.

Clause 14. The catheter of Clause 13, wherein the first echogenic member is a first size, and wherein the second echogenic member is a second size different than the first size.

Clause 15. The catheter of Clause 13 or 14, wherein the first echogenic member is a first shape, and wherein the second echogenic member is a second shape different than the first shape.

Clause 16. The catheter of any one of Clauses 13 through 15, wherein the second echogenic member is within a range from about 5 mm to about 25 mm proximal to the first echogenic member.

Clause 17. The catheter of any one of Clauses 1 through 16, wherein the lumen is configured to receive an implantable medical electrical lead comprising at least one electrode.

Clause 18. The catheter of any one of Clauses 1 through 17, wherein the distal end of the elongate body is configured to receive an implantable medical device.

Clause 19. The catheter of any one of Clauses 1 through 18, wherein the soundwave comprises an ultrasonic soundwave having a frequency within range from about 1 megahertz (MHz) to about 20 MHz.

Clause 20. The catheter of any one of Clauses 1 through 19, further comprising a handle assembly having a control member, wherein the handle assembly is configured to controllably expand the echogenic member from the collapsed configuration to the expanded configuration.

Clause 21. A kit comprising: a catheter comprising: an elongate body extending along a longitudinal axis from a proximal end to a distal end and defining a lumen extending longitudinally within the elongate body, the elongate body comprising a proximal portion and a distal portion; and an echogenic member positioned on the distal portion of the elongate body, wherein the echogenic member is configured to controllably expand from a collapsed configuration to an expanded configuration, and wherein the echogenic member is configured to diffusely scatter a soundwave; and a medical device sized for delivery out of the distal end of the elongate body and configured for at least one of therapy delivery or sensing.

Clause 22. The kit of Clause 21, wherein the echogenic member comprises an echogenic coating.

Clause 23. The kit of Clause 21 or 22, further comprising an echogenic fluid, wherein the echogenic member is configured to be inflated with the echogenic fluid.

Clause 24. The kit of any one of Clauses 21 through 23, wherein the echogenic member comprises a first echogenic member, wherein the catheter further comprises a second echogenic member proximal to the first echogenic member on the distal portion of the elongate body.

Clause 25. The kit of any one of Clauses 21 through 24, wherein the medical device comprises at least one of a medical electrical lead or an implantable medical device.

Clause 26. The kit of any one of Clauses 21 through 25, wherein the catheter further comprises a handle assembly configured to controllably expand the echogenic member from the collapsed configuration to the expanded configuration.

Clause 27. A method comprising: advancing a catheter toward a selected location within a patient, wherein the catheter comprises: an elongate body extending along a longitudinal axis from a proximal end to a distal end and defining a lumen extending longitudinally within the elongate body, the elongate body comprising a proximal portion and a distal portion; and an echogenic member positioned on the distal portion of the elongate body, expanding the echogenic member from a collapsed configuration to an expanded configuration, wherein the echogenic member is configured to diffusely scatter a soundwave; identifying at least one of a position, an orientation, or a trajectory of the distal portion of the catheter relative to the selected location based on a soundwave reflected by the echogenic member; and advancing a medical device through the lumen and out the distal end of the elongate body to the selected location for at least one of therapy delivery or sensing.

Clause 28. The method of Clause 27, wherein expanding the echogenic member comprises injecting a fluid into the echogenic member.

Clause 29. The method of Clause 27, wherein the catheter further comprises a handle having a control member coupled to a pull wire, and wherein expanding the echogenic member comprises actuating the control member to cause the pull wire to expand the echogenic member.

Clause 30. The method of any one of Clauses 27 through 29, wherein identifying at least one of the position, the orientation, or the trajectory of the distal portion comprises: imaging, by an ultrasound imaging device, the at least one echogenic member; and determining, based on the ultrasound image, at least one of the position, the orientation, or the trajectory of the distal portion relative to an anatomy of the patient surrounding the distal portion of the catheter.

Clause 31. A method comprising: forming an elongate body extending along a longitudinal axis from a proximal end to a distal end and defining a lumen extending longitudinally within the elongate body, the elongate body comprising a proximal portion and a distal portion, wherein the lumen is configured to receive a medical device for at least one of therapy delivery or sensing; and forming, on the distal portion of the elongate body, an echogenic member configured to controllably expand from a collapsed configuration to an expanded configuration, wherein the echogenic member is configured to diffusely scatter a soundwave.

Clause 32. The method of Clause 31, wherein forming the echogenic member comprises applying an echogenic coating to the echogenic member.

Various examples of the disclosure have been described. Any combination of the described systems, operations, or functions is contemplated. These and other examples are within the scope of the following claims.

What is claimed is:

1. A catheter comprising:
   an elongate body extending along a longitudinal axis from a proximal end to a distal end and defining a lumen extending longitudinally within the elongate body, the elongate body comprising a proximal portion and a distal portion; and
   an echogenic member having, in an expanded configuration, at least one of a shape or a size determined by at least one of an axial resolution, a lateral resolution, or an elevational resolution of an ultrasound device, the echogenic member being positioned on the distal portion of the elongate body, wherein the echogenic member is configured to controllably expand from a collapsed configuration to the expanded configuration, and wherein the echogenic member is configured to diffusely scatter a soundwave.

2. The catheter of claim 1, wherein the echogenic member comprises a balloon inflatable from the collapsed configuration to the expanded configuration and deflatable from the expanded configuration to the collapsed configuration.

3. The catheter of claim 1, wherein the echogenic member comprises at least one of a self-expanding member or controllably expanding member.

4. The catheter of claim 1, wherein, when in the collapsed configuration, a diameter of the echogenic member is less than about 9.5 millimeters (mm).

5. The catheter of claim 1, wherein, when in the expanded configuration, a diameter of the echogenic member is within a range between about 1 mm and about 30 mm.

6. The catheter of claim 1, wherein the echogenic member is positioned between about 0 mm and about 5 mm from the distal end of the elongate body.

7. The catheter of claim 1, wherein the shape of the echogenic member is selected from the group including a sphere, an ellipse, and a frustum.

8. The catheter of claim 1, wherein the echogenic member comprises a distal end and a proximal end, each coupled to an external surface of the elongate member, wherein the echogenic member is tapered toward the longitudinal axis at one or more of the distal end or the proximal end of the echogenic member.

9. The catheter of claim 1, wherein the echogenic member comprises an echogenic coating.

10. The catheter of claim 9, wherein the echogenic coating comprises an echogenic polymer.

11. The catheter of claim 10, wherein the echogenic member is configured to be inflated with an echogenic fluid.

12. The catheter of claim 1, further comprising a radiopaque marker on the distal portion of the elongate body.

13. The catheter of claim 1, wherein the echogenic member comprises a first echogenic member, wherein the catheter further comprises a second echogenic member proximal to the first echogenic member on the distal portion of the elongate body.

14. The catheter of claim 13, wherein the first echogenic member is a first size, and wherein the second echogenic member is a second size different than the first size.

15. The catheter of claim 13, wherein the first echogenic member is a first shape, and wherein the second echogenic member is a second shape different than the first shape.

16. The catheter of claim 13, wherein the second echogenic member is within a range from about 5 mm to about 25 mm proximal to the first echogenic member.

17. The catheter of claim 1, wherein the lumen is configured to receive an implantable medical electrical lead comprising at least one electrode.

18. The catheter of claim 1, wherein the distal end of the elongate body is configured to receive an implantable medical device.

19. The catheter of claim 1, wherein the soundwave comprises an ultrasonic soundwave having a frequency within a range from about 1 megahertz (MHz) to about 20 MHz.

20. The catheter of claim 1, further comprising a handle assembly having a control member, wherein the handle assembly is configured to controllably expand the echogenic member from the collapsed configuration to the expanded configuration.

21. A kit comprising:
   a catheter comprising:

an elongate body extending along a longitudinal axis from a proximal end to a distal end and defining a lumen extending longitudinally within the elongate body, the elongate body comprising a proximal portion and a distal portion; and an echogenic member having, in an expanded configuration, at least one of a shape or a size determined by at least one of an axial resolution, a lateral resolution, or an elevational resolution of an ultrasound device, the echogenic member being positioned on the distal portion of the elongate body, wherein the echogenic member is configured to controllably expand from a collapsed configuration to the expanded configuration, and wherein the echogenic member is configured to diffusely scatter a soundwave; and a medical device sized for delivery out of the distal end of the elongate body and configured for at least one of therapy delivery or sensing.

22. The kit of claim 21, wherein the echogenic member comprises an echogenic coating.

23. The kit of claim 21, further comprising an echogenic fluid, wherein the echogenic member is configured to be inflated with the echogenic fluid.

24. The kit of claim 21, wherein the echogenic member comprises a first echogenic member, wherein the catheter further comprises a second echogenic member proximal to the first echogenic member on the distal portion of the elongate body.

25. The kit of claim 21, wherein the medical device comprises at least one of a medical electrical lead or an implantable medical device.

26. The kit of claim 21, wherein the catheter further comprises a handle assembly configured to controllably expand the echogenic member from the collapsed configuration to the expanded configuration.

27. A method comprising:
advancing a catheter toward a selected location within a patient, wherein the catheter comprises:
an elongate body extending along a longitudinal axis from a proximal end to a distal end and defining a lumen extending longitudinally within the elongate body, the elongate body comprising a proximal portion and a distal portion; and
an echogenic member positioned on the distal portion of the elongate body;
the method further comprising:
determining at least one of a shape or a size of the echogenic member in an expanded configuration of the echogenic member, based on at least one of an axial resolution, a lateral resolution, or an elevational resolution of an ultrasound device;
expanding the echogenic member from a collapsed configuration to the expanded configuration, wherein the echogenic member is configured to diffusely scatter a soundwave;
identifying at least one of a position, an orientation, or a trajectory of the distal portion of the catheter relative to the selected location based on a soundwave reflected by the echogenic member; and
advancing a medical device through the lumen and out the distal end of the elongate body to the selected location for at least one of therapy delivery or sensing.

28. The method of claim 27, wherein expanding the echogenic member comprises injecting a fluid into the echogenic member.

29. The method of claim 27, wherein the catheter further comprises a handle having a control member coupled to a pull wire, and wherein expanding the echogenic member comprises actuating the control member to cause the pull wire to expand the echogenic member.

30. The method of claim 27, wherein identifying at least one of the position, the orientation, or the trajectory of the distal portion comprises:
imaging, by the ultrasound device, the echogenic member; and
determining, based on an ultrasound image produced by the ultrasound device, at least one of the position, the orientation, or the trajectory of the distal portion relative to an anatomy of the patient surrounding the distal portion of the catheter.

31. A method comprising:
forming an elongate body extending along a longitudinal axis from a proximal end to a distal end and defining a lumen extending longitudinally within the elongate body, the elongate body comprising a proximal portion and a distal portion, wherein the lumen is configured to receive a medical device for at least one of therapy delivery or sensing;
forming, on the distal portion of the elongate body, an echogenic member configured to controllably expand from a collapsed configuration to an expanded configuration, wherein the echogenic member is configured to diffusely scatter a soundwave; and
determining at least one of a shape or a size of the echogenic member in the expanded configuration, based on at least one of an axial resolution, a lateral resolution, or an elevational resolution of an ultrasound device.

32. The method of claim 31, wherein forming the echogenic member comprises applying an echogenic coating to the echogenic member.

* * * * *